Figure 1:
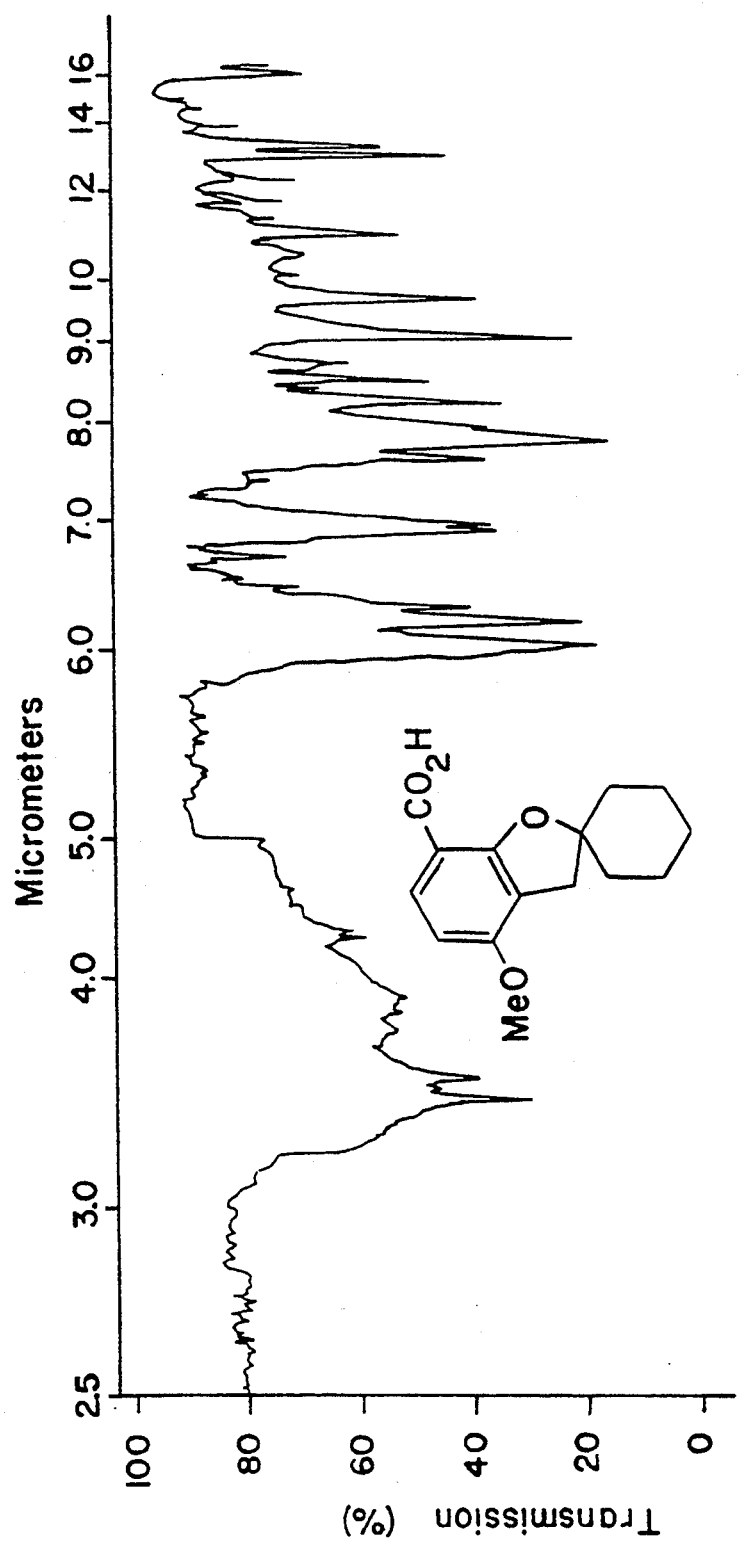

United States Patent [19]

Sindelar et al.

[11] Patent Number: 5,401,767
[45] Date of Patent: Mar. 28, 1995

[54] COMPOUNDS WHICH INHIBIT COMPLEMENT AND/OR SUPPRESS IMMUNE ACTIVITY

[75] Inventors: Robert D. Sindelar, Oxford, Miss.; Barton J. Bradbury, West Chester, Ohio; Teodoro Kaufman, Rosario, Argentina; Stephen H. Ip, Sudbury; Henry C. Marsh, Jr., Reading, both of Mass.

[73] Assignees: T Cell Sciences, Inc., Needham, Mass.; The University of Mississippi, University, Miss.

[21] Appl. No.: 997,266

[22] Filed: Dec. 21, 1992

Related U.S. Application Data

[62] Division of Ser. No. 182,275, Apr. 15, 1988, Pat. No. 5,173,499.

[51] Int. Cl.$^6$ .................. A61K 31/335; A61K 31/34; A61K 31/16
[52] U.S. Cl. .................... 514/462; 514/470; 514/468; 514/615; 514/885; 549/345
[58] Field of Search ............... 514/462, 420, 315, 468, 514/885, 469, 461; 549/345, 429, 468

[56] References Cited

U.S. PATENT DOCUMENTS

| | | | |
|---|---|---|---|
| 3,128,286 | 4/1964 | Walker et al. | 260/346.2 |
| 3,518,283 | 6/1970 | Brossi et al. | 260/346.2 |
| 4,035,509 | 7/1977 | Nelson et al. | |
| 4,229,466 | 10/1980 | Miyazaki et al. | 424/279 |
| 4,263,317 | 4/1981 | Martin et al. | 548/278 |
| 4,268,516 | 5/1981 | Lombardino et al. | 424/273 |
| 4,301,292 | 11/1981 | Martin et al. | 548/239 |

(List continued on next page.)

FOREIGN PATENT DOCUMENTS

| | | |
|---|---|---|
| 867095 | 11/1978 | Belgium . |
| 2821403 | 1/1979 | Germany . |
| 3031788 | 3/1981 | Germany . |
| 54-37832 | 3/1979 | Japan . |
| 54-92680 | 7/1979 | Japan . |

(List continued on next page.)

OTHER PUBLICATIONS

Hong et al., 1979, "An anti-complementary agent, K-76 monocarboxylic acid: Its site and mechanism of inhibition of the complement activation cascade," J. Immunol., 122:2418.

Hong et al., 1981, "Inhibitory effect of K-76 monocarboxylic acid, an anticomplementary agent, on the C3b inactivator system," J. Immunol., 127:104.

Hong et al., 1981, "Simple methods for preparing EAC1, 4b, 2a, 3b, and EAC4b, 3b with human or guinea pig complement components using an anticomplementary agent, K-76 monocarboxylic acid," J. Immunol., 127:109.

Bumpers and Baum, 1983, "The effect of a novel C5 inhibitor (K-76 CONNa) on tumor cell chemotaxis," J. Lab. Clin. Med., 102:421.

Konno and Tsunifugi, 1983, "Induction of zymosan air pouch inflammation in rats and its characterization with reference to the effects of anticomplementary and anti--inflammatory agents," Dr. J. Pharmacol., 80:269.

(List continued on next page.)

Primary Examiner—Raymond J. Henley, III
Assistant Examiner—T. J. Criares
Attorney, Agent, or Firm—Pennie & Edmonds

[57] ABSTRACT

The present invention is directed to compounds which suppress immune responses and/or selectively inhibit complement. These compounds contain an aromatic ring and are substituted dihydrobenzofurans, spirobenzofuran-2(3H)-cycloalkanes, and their open chain intermediates. The compounds of the present invention, and the pharmaceutically acceptable salts thereof, interrupt the proteolytic processing of C5 to bioactive components, exhibit immunosuppressive activities, and have therapeutic utility in the amelioration of disease and disorders mediated by complement and/or immune activity.

18 Claims, 7 Drawing Sheets

U.S. PATENT DOCUMENTS

| | | | |
|---|---|---|---|
| 4,404,221 | 9/1983 | Giamkowski et al. | 424/285 |
| 4,426,380 | 1/1984 | Wenk et al. | 424/244 |
| 4,451,462 | 5/1984 | Wenk et al. | 424/248.55 |
| 4,517,311 | 5/1985 | Giamkowski et al. | 514/462 |
| 4,558,043 | 12/1985 | Wenk et al. | 514/210 |

(List continued on next page.)

FOREIGN PATENT DOCUMENTS

| | | |
|---|---|---|
| 54-106458 | 8/1979 | Japan . |
| 57-83281 | 5/1982 | Japan . |
| 57-83282 | 5/1982 | Japan . |
| 9210205 | 6/1962 | WIPO . |

OTHER PUBLICATIONS

Miyazaki et al., 1983, "Complement inhibitor, K-76 COOH," Farumashia (Japan) 19:912.

Ramm et al., 1983, "Size distribution and stability of the trans-membrane channels formed by complement complex C5b-9," Mol. Immunol., 20:155.

Hudig et al., 1984, "Inhibition of human lymphocyte natural cytotoxicity and antibody-dependent cell-mediated cytotoxicity by K-76 COONa, a reagent that blocks complement activity," J. Immunol., 133:408.

Miyazaki et al., 1984, "Effects of K-76 monocarboxylic acid, an anticomplementary agent, in various in vivo immunological reactions and on experimental glomerulonaphritis," Complement 1:134.

Rudelman et al., 1984, "The mechanism of cell-mediated cytotoxicity, II. K-76 COONa, which inhibits the activity of Factor I and CS, inhibits early events in cytotoxic T-lymphocyte-mediated cytolysis and in T-lymphocyte activation," Cell Immunol., 88:16.

Kanno and Tsurufugi, 1985, "Inhibitory effect of a novel anti-complementary agent, K-76 COONa, on the release of histamine induced by zymosan and compound 48/80," Jpn. J. Pharmacol., 38:116.

Redelman et al., 1986, "The induction of human T-cell growth factor receptor precedes the reduction of RNA and occurs in the presence of inhibitors of RNA synthesis," Cytometry 7:453.

Iida et al., 1987, "Effect of the anticomplementary agent, K-76 monocarboxylic acid on experimental immune complex glomerulonephritis in rats," Clin. Exp. Immunol., 67:130.

Miyazaki et al., 1980, "A complement inhibitor produced by *Stachybotrys complementi*, nov. sp. K-76, a new species of fungi imperfecti," Microbiol. Immunol., 24(11):1091.

Kaise et al., 1979, "Structure of K-76, a complement inhibitor produced by *Stachybotrys complementi* nov. sp. K-76," J. Chem. Soc. Chem. Commun., 726.

McMurry and Erion, 1985, "Stereoselective total synthesis of the complement inhibitor K-76," J. Am. Chem. Soc., 107:2712.

Corey and Das, 1982, "Total synthesis of the complement inhibitor K-76 in racemic form. Structural assignment to K-76 monocarboxylic acid," J. Am. Chem. Soc., 104:5551.

Spanevello et al., 1982, "Regioselective synthesis of the spiro-benzofuran unit, present in several natural products, by an intramolecular Michael cyclization," Syn. Commun. 16(7):749.

Sullivan et al., 1981, "Antimicrobial constituents of the sponge *Siphonodictyon coralliphagum*," Tetrahedron 37:979.

Dave et al., 1984, "A piscicidal chromanol and a chromenol from the brown alga *Dictyopteris undulata*," Heterocycles 22(10):2301.

Gerwick and Fenical, 1981, "Ichthyotoxic and cytotoxic metabolites of the tropical brown alga *Stypopodium zonale* (Lamouroux) papenfuss," J. Org. Chem., 46:22.

Brandt et al., 1972, "Structure and synthesis of crombenin, a natural spirocoumaranone," J. Chem. Soc. Chem. Commun., 392.

Antua et al., 1986, "Synthesis of Grisan," Tetrahedron 42(20):5637.

Kazlauskas et al., 1978, "New quinones from a dictyoceratid sponge," Aus. J. Chem., 31:2685.

Jackson and Short, 1937, "Anisoxide. Part I," J. Chem. Soc., 513.

Grove et al., 1952, "Griseofulvin. Part IV," J. Chem. Soc., 3977.

Oxford et al., 1935, "CXXXIX. Studies in the biochem- (List continued on next page.)

U.S. PATENT DOCUMENTS

| | | | |
|---|---|---|---|
| 4,647,677 | 3/1987 | Tamura et al. | 549/462 |
| 4,740,519 | 4/1988 | Shroot et al. | 514/443 |
| 4,857,516 | 8/1989 | Terao et al. | 514/100 |
| 4,863,958 | 9/1989 | Belanger et al. | 514/469 |
| 5,173,499 | 12/1992 | Sindelar et al. | 514/462 |

OTHER PUBLICATIONS istry of microorganisms. XLIV. Fulvic acid, a new crystalline yellow pigment, a metabolic product of P. griseofulvum dierckx, P. Flexuosum dale and P. Brefeldianum dodge," Biochem J., 29:1102.

Weinberg, 1981, "Principles of medicinal chemistry," 2d. Ed. Foye, W. O., ed., Lea and Febiger, Philadelphia, Pa. p. 813.

Closse et al., 1981, "2,3-dihydrobenzofuran-2-one: A new class of highly potent antinflammatory agents," J. Med. Chem., 24:1465.

Hammond et al., 1989, "2,3-dihydro-5-benzofuranols as antioxidant-based inhibitors of leukotriene biosynthesis," J. Med. Chem., 32:1006.

Kruse et al., 1981, "Synthesis of spiro[isobenzofuran-1(3H), 4'-piperidines] as potential central nervous system agents. 6. Synthesis, C-13 NMR, and biological evaluation of cis- and trans-4-amino-3'-arylspiro-[cyclohexane-1,1'(3'H)-isobenzofuran] derivatives," J. Med. Chem. 24:617.

Narasimhan and Mali, 1983, "Synthesis of heterocyclic compounds involving aromatic lithiation reactions in the key step," Synthesis, 957.

Townsend and Bloom 1981, "Studies on methoxymethyl-directed metalation," Tet. Lett. 22:3923.

Ronald, 1975, "Methoxymethyl ethers, an activating group for rapid and regioselective metalation," Tet. Lett. 46:3973.

Lielbriedis and Gudriniece, 1968, "Diketone-based heterocyclic compounds," Latv. PSR Zinat. Akad. Vestis, Kim. Ser. 2:192.

Scholz et al., 1982, "Preparation and study of some transformations in 1(4H)-naphthalenone," Bol. Soc. Chil. Quim. 27(2):129.

Becker et al., 1983, "Chemotactic factors of inflammation," Trends Pharmacol. Sci., 4:223.

Becker, 1967, "The relationship of the structure of phosphonate esters to their ability to inhibit chymotrypsin, trypsin, acetylcholinesterase and C'ia," Biochim. Biophys. Acta., 147:289.

Bradbury and Sindelar, 1989, "Synthesis of 4,7-disubstituted spirobenzofuran-2(3H)-cyclohexanes," J. Heterocyclic Chem., 26:1827.

Bult and Herman, 1983, "Inflammatory mediators released by complement-derived peptides," Agents and Actions 13(5/6):405.

Burge et al., 1978, "Inhibition of the alternative pathway of complement by gold sodium thiomalate in vitro," J. Immunol., 120(5):1625.

Cavarocchi et al., 1986, "Oxygen free radical generation during cardiopulmonary bypass: correlation with complement activation," Circulation 74(suppl.III):130.

Crawford et al., 1972, "Metalation of limonene. A novel method for the synthesis of bisabolane sesquiterpenes," J. Am. Chem. Soc., 94:4298.

Djura and Sargent, 1983, "The structure of isopannarin," Aust. J. Chem., 36:1057.

Eisen, 1979, "Cell-mediated hypersensitivity and immunity," Immunology Ch. 20, Harper and Row, Hagerstown, Md., p. 558.

Eisen et al., 1974, "Complement," Immunology Ch. 18, Harper and Row, Publishers Inc., Hagerstown, Md., p. 512.

Fugi et al., 1979, "Hard acid and soft nucleophile system. New efficient method for removal of benzyl protecting group," J. Org. Chem., 44(10):1661.

Fujimoto et al., 1983, "Spontaneous release of the Leu-2 (T8) molecule from human T cells", J. Exp. Med., 159:752.

Fujita et al., 1976, "Biosynthesis of natural products. Part 1. Incorporation of ent-kaur-16-ene and ent-kaur-16-en-15-one into enmein and oridonin," J. Chem. Soc., 23:2098.

Glovsky et al., 1969, "Role of fumaropimaric acid in guinea pig complement dependent and non-complement dependent biologic reactions," J. Immunol., 102(1):1.

(List continued on next page.)

OTHER PUBLICATIONS

Grieco et al., 1975, "Model studies directed toward the total synthesis of vernolepin. III. Synthesis of the α-methylene-δ-valerolactone AB ring model," J. Org. Chem., 40(10):1450.

Gschwend and Rodriguez, 1979, "Heteroatom-facilitated lithiations," Org. React., 26:1.

Hansch and Yoshimoto, 1974, "Structure-activity relationships in immunochemistry. 2. Inhibition of complement by benzamidines," J. Med. Chem., 17(11):1160.

Hood et al., 1984, "Antigen-bound IgM and IgG antibodies initiate complement fixation," Immunology, 2d ed.. The Benjamin/Cummings Publishing Co., Menlo Park, Calif., p. 339.

Hugli, 1981, "The structural basis for anaphylatoxin and chemotactic functions of C3a, C4a, and C5a," CRC Crit. Rev. Immunol., 1:321.

Johnson et al., 1975, "Release of histamine from rat mast cells by the complement peptides C3a and C5a," Immunology 28:1067.

Jolly et al., 1986, "Reduction of myocardial infarct size by neutrophil depletion: Effect of duration of occlusion," Am. Heart J., 112(4):682.

Kaufman and Sindelar, 1989, "A short and efficient synthesis of grisan," J. Heterocyclic Chem., 26:879.

Kaufman et al., 1989, "$^{13}$C NMR chemical shifts of the carbon atoms of the methoxymethyl group of di-ortho-substituted aromatic methoxymethyl ethers," J. Heterocyclic Chem. 27:1178.

Kirklin et al., 1983, "Complement and the damaging effects of cardiopulmonary bypass," J. Thorac. Cardiovasc. Surg., 86:845.

Lythgoe et al., 1956, "Calciferol and its relatives. Part II. An alternative synthesis of trans-1,2′cyclohexylidene-ethylidene-2-methylenecyclohexane," J. Chem Soc., Part IV:4060–4065.

Meuer et al., 1984, "Triggering of the T3-Ti antigen-receptor complex results in clonal T-cell proliferation through an interleukin 2-dependent autocrine pathway," Proc. Natl. Acad. Sci. USA 81:1509.

Miescher and Muller-Eberhard, 1976, Text Book of Immunopathology, 2d ed., vols. I and II, Grune and Stratton, New York.

Miller et al., 1980, "Synthesis and enzymatic and inotropic activity of some new 8-substituted and 6,8-disubstituted derivatives of adenosine cyclic 3′,5′-monophosphate," J. Med. Chem., 23:242.

Mori and Komatsu, 1988, "Synthesis of the complement inhibitor (−)-K-76 and of related compounds," Liebigs Ann. Chem., pp. 107–119.

Muller-Eberhard, 1978, "Complement: Molecular mechanisms, regulation and biologic function," Molecular Basis of Biological Degradative Processes, Berlin, R. D. et al., eds. Academic Press, N.Y., p. 65.

Narasimhan et al., 1979, "Synthetic application of lithiation reactions; Part XIII. Synthesis of 3-phenylcoumarins and their benzo derivatives," Synthesis, p. 906.

Rall et al., 1976, "Crown ethers. Application in the synthesis of chalcones," Tetrahedron Letters No. 13, p. 1033.

Rapp and Borsos, 1970, Molecular Basis of Complement Action, Appleton-Centuury-Crofts (Meredith Corp.), New York.

Regal and Pickering, 1983, "C5a and antigen-induced tracheal contraction: Effect of a combination of an antihistamine and cyclo-oxygenase inhibitors," Int. J. Immunopharmac., 5(1):71.

Rossen et al., 1985, "Selective accumulation of the first component of complement and leukocytes in ischemic canine heart muscle," Circulation Research 57(1):119.

Rubin et al., 1985, "Soluble interleukin-2 receptors are shed by activated human lymphocytes in vitro," Fed. Proc., 44:946 (Abstract No. 3131).

Rubin et al., 1985, "Soluble interleukin 2 receptors are released from activated human lymphoid cells in vitro," J. Immunol., 135(5):3172.

Sandberg, 1981, "Complement," in Cellular Functions in Immunity and Inflammation, Oppenheim, J. J. et al., eds., Elsevier/North Holland, N.Y., p. 373.

Schafer et al., 1986, "Deposition of the terminal C5b-9 complement complex in infarcted areas of human myocardium," J. Immunol., 137(6):1945.

Simpson and Lucchesi, 1987, "Free radicals and myocardial ischemia and reperfusion injury," J. Lab. Clin Med., 110(1):13.

Tack et al., 1979, "Fifth component of human complement: Purification from plasma and polypeptide chain structure," Biochemistry 18(8):1490.

Takada et al., 1978, "Inhibition of the classical and (List continued on next page.)

OTHER PUBLICATIONS alternative pathways by amino acids and their derivatives," Immunology 34:509.

Tsudo et al., 1984, "Expression of tac antigen on activated normal human B cells," J. Exp. Med., 160:612.

Vogt et al., 1979, "Interference of propamidine with binding of the fifth component of complement to surface–fixed C3b, and with C5 activation," Immunology 36:139.

Waldmann et al., 1984, "Expression of interleukin 2 receptors on activated human B cells," J. Exp. Med., 160:1450.

Webster et al., 1980, "Biological effects of the human complement fragments C5a and C5a (desarg) on neutrophil function," Immunopharmacol., 2:201.

Wheeler and Lerner, 1956, "Structure and Properties of cyclic compounds. III. Dissociation constants of simple $\alpha,\beta$–unsaturated cyclic acids," J. Am. Chem. Soc., 78:63.

WHO Scientific Group, 1977, "Chemotherapy of solid tumours," WHO Tech. Rep. Ser., 606:3.

Wissler, 1972, "Chemistry and Biology of the anaphylatoxin related serum peptide system," Eur. J. Immunol., 2:73.

Bradbury and Sindelar, 1987, "Synthesis and evaluation of partial derivatives of the complement inhibitor K–76," 14th Annual Malto Medicinal Chemistry-Pharmacognosy Meeting, May 17–19, Abstract Only.

Bradbury and Sindelar, 1987, "Synthesis of 4,7–disubstituted spirobenzofuran–2(3H)–cyclohexanes," National American Chemical Society 194th Meeting, Sep. 4, New Orleans, La., Abstract Only.

Sindelar et al., 1990, "Potential complement inhibitors blocking release of C5a based on a natural product model," American Chemical Society Division of Medicinal Chemistry, 200th ACS National Meeting, Aug. 26–31, Washington D.C., Abstract No. 178.

Sindelar et al., 1989, "Synthesis and evaluation of B/C/D–ring analogues of the anti–complement natural product K–76," American Chemical Society National 198th Meeting Sep. 10, Miami, Fla., Abstract No. 35.

Sindelar et al., 1988, "Synthesis of A/C/D–ring analogues of the anticomplement natural product K–76," American Chemical Society 196th National Meeting, Sep. 29, Los Angeles, Calif., Abstract Only.

Sindelar et al., 1988, "Synthesis and evaluation of B/C/D–ring analogues of the natural product complement inhibitor K–76," American Association of Pharmaceutical Scientists, AAPS Meeting Nov. 2, Orlando, Fla., Abstract Only.

Morrison et al., 1990, "Formation of 2,2–Spiro–Substituted 2,3–dihydrobenzo furans" Chemical Abstracts, vol. 112, No. 5, Abstract No. 355916.

Bradbury et al., 1989, "Synthesis of 4,7–Disubstituted Spiro benzo furan –2(H)–Cyclohexanes, Journal of Heterocyclic Chemistry, vol. 26, No. 6, p. 1827.

COMPOUNDS WHICH INHIBIT COMPLEMENT AND/OR SUPPRESS IMMUNE ACTIVITY

This application is a divisional of application 07/182,275, filed Apr. 15, 1988, now U.S. Pat. No. 5,173,499.

TABLE OF CONTENTS

1. Field of the Invention
2. Background of the Invention
   2.1. The Complement System
   2.2. Cell-Mediated Immune Responses
   2.3. Compounds Which Inhibit Complement
   2.4. Spirobenzofuran-2 (3H)-cycloalkanes and K-76
3. Summary of the Invention
   3.1. Definitions
4. Brief Description of the Figures
5. Detailed Description of the Invention
   5.1. Compounds Which Inhibit Complement and/or Suppress Immune Activity
   5.2. Synthetic Processes
      5.2.1. Preparation of Compounds of the General Formula 5
      5.2.2. Preparation of Compounds of the General Formulae (3 and 4)
   5.3. Demonstration of Complement Inhibition
   5.4. Demonstration of Immunosuppressive Activity
   5.5. Therapeutic Uses of the Compounds of the Invention
6. Examples
   6.1. 4-(1'-Cyclohexenyl)methyl-3,5-dimethoxybenzyl alcohol (13c)
   6.2. 2-(1'-Cyclohexenyl)methyl-3-methoxymethoxyanisole (9a)
   6.3. 3-(1'-Cyclohexenyl)methyl-2-hydroxy-4-methoxybenzoic acid (12a)
   6.4. 3-(1'-Cyclohexenyl)methyl-2-hydroxy-4-methoxybenzaldehyde (12b)
   6.5. 3-(1'-Cyclohexenyl)methyl-2-methoxymethoxy-4-methoxy-N-methylbenzamide (10b) and -N-tert-butylbenzamide (10c)
   6.6 3-(1'-Cyclohexenyl)methyl-4-methoxy-2-methoxymethoxybenzyl Alcohol (10d)
   6.7. 7-Carboxyl-4-methoxyspiro[benzofuran-2(3H)-cyclohexane] (11a)
   6.8. 7-Formyl-4-methoxyspiro[benzofuran-2(3H)-cyclohexane] (11b)
   6.9. 4-Methoxyspiro[benzofuran-2(3H)-cyclohexane]7-N-methylcarboxamide (11c)
   6.10. 7-Carboxyl-4-hydroxyspiro[benzofuran 2(3H)-cyclohexane] (14a)
   6.11. 7-Formyl-4-hydroxyspiro[benzofuran-2(3H)-cyclohexane] (14b)
   6.12. 4-(1'-Cyclohexenyl)methyl-3,5-dimethoxybenzaldehyde (13b)
   6.13. 4-(1'-Cyclohexenyl)methyl-3-hydroxy-5-methoxybenzaldehyde (15b) and 4-(1'-cyclohexenyl)methyl-3-hydroxy-5methoxybenzoic acid (15a)
   6.14. 6-Carboxyl-4-methoxyspiro[benzofuran-2(3H) cyclohexane] (30a) and 6-formyl-4-methoxyspiro[benzofuran -2(3H)-cyclohexane] (30b)
   6.15. 6-Formyl-4-hydroxyspiro[benzofuran-2(3H) cyclohexane] (31b) and 6-carboxyl-4-hydroxyspiro[benzofuran-2(3H)-cyclohexane] (31a)
   6.16. (+)-1-Methoxy-3-methoxymethoxy-2-[2-(4'-methylcyclohex-3'-en-1'R-yl)prop-2-enyl]benzene ((+)-9b) and ((−)-9b)
   6.17. 4-R-(+)-(3-Chloropropen-2-yl)-1-methyl -1S, 2R-cyclohexanediol acetonide ((+)-6c)
   6.18. (+)-1-methoxy-3-methoxymethoxy-2-[2-(3'R, 4'S-dihydroxyacetonide-4'-methylcyclohex 1'R-yl}prop-2-enyl]benzene ((+)-9c)
   6.19. (+)-2-Hydroxy-4-methoxy-3-[2-(4'-methylcyclo-hex -3'-en-1'R-yl}prop-2-enyl]benzoic acid ((+)-22a) and ((−)-22a)
   6.20. (+)-4-Methoxy-2-methoxymethoxy-3-[2(4'-methylcyclohex-3'-en-1'R-yl}prop-2-enyl]benzaldehyde ((+)-21b) and ((−)-21b)
   6.21. (+)-2-Hydroxy-4-methoxy-3-[2-{4'-methylcyclo -hex-3'-en-1'R-yl}prop-2-enyl]benzaldehyde ((+)-22b) and ((−)-22b)
   6.22. Ethyl (+)-4-methoxy-2-methoxymethoxy-3-[2-(4'-methylcyclohex-3'-en-1'R-yl}prop-2enyl]benzoate ((+)-21c) and ((−)-21c)
   6.23. Ethyl (+)-2-hydroxy-4-methoxy-3-[2-{4'-methylcyclohex -3'-en-1'R-yl}prop-2-enyl]benzoate ((+)-22c) and ((−)-22c)
   6.24. Ethyl (+)-4-methoxy-2-methoxymethoxy-3 [2-(3'R, 4'S-dihydroxyacetonide-4'-methylcyclohex-1'R-yl}prop-2-enyl]benzoate ((+)-25c)
   6.25. (+)-4-Methoxy-2-methoxymethoxy-3-[2(3'R, 4'S-dihydroxyacetonide-4'-methylcyclohex-1'R-yl)prop-2-enyl]benzaldehyde ((+)-25b)
   6.26. (+)-2-Hydroxy-4-methoxy-3-[2-(3'R, 4'S-dihydroxy-4'-methylcyclohex-1'R-yl) prop-2-enyl]benzaldehyde ((+)-26b) and Ethyl (+)-2-hydroxy-4-methoxy-3-[2-(3'R, 4'S-dihydroxy-4'-methylcyclohex-1'R-yl) prop-2-enyl]benzoate ((+)-26c)
   6.27. (+)-7-Carboxyl-4-methoxy-2-methyl-2-[4'-methylcyclohex-3'-en-1'R-yl]-(3H)-benzofuran ((+)-20a) and ((−)-20a)
   6.28. (+)-7-Formyl-4-methoxy-2-methyl-2-[4'-methylcyclohex -3'-en-1'R-yl]-(3H)-benzofuran ((+)-20b) and ((−)-20b)
   6.29. (+)-7-Carbethoxy-4-methoxy-2-methyl -2-[4'-methylcyclohex-3'-en-1'R-yl]-(3H)-benzofuran ((+)-20c) and ((−)-20c)
   6.30. (+)-7-Formyl-4-methoxy-2-methyl-2 [3'R, 4'S-dihydroxy-4'-methylcyclohex -1'R-yl 3-(3H)-benzofuran ((+)-27b); (+)-7-carbethoxy-4-methoxy-2-methyl-2-[3'R, 4'S-dihydroxy-4'-methylcyclohex -1'R-yl]-(3H)-benzofuran ((+)-27c), and (+)-7-carboxyl-4-methoxy-2-methyl-2-[3'R, 4'S-dihydroxy-4'-methylcyclohex -1'R-yl]-(3H)-benzofuran ((+)-27a)
   6.31. (+)-7-Formyl-4-hydroxy-2-methyl -2-[4'-methylcyclohex-3'-en-1'R-yl]-(3H) -benzofuran ((+)-23b) and ((−)-23b)
   6.32. (+)-7-Carbethoxy-4-hydroxy-2-methyl -2-[4'-methylcyclohex-3'-en-1'R-yl]-(3H) -benzofuran ((+)-23c) and ((−)-23c)
   6.33. (+)-7-Carboxyl-4-hydroxy-2-methyl -2-[4'-methylcyclohex-3'-en-1'R-yl ]-(3H) -benzofuran ((+)-23a) and ((−)-23a)
   6.34. (+)-7-Formyl-4-hydroxy-2-methyl -2-[3'R ,4'S-dihydroxy-4'-methylcyclohex -1'R-yl]-(3H)-benzofuran ((+)-24b) and (+)-7-carbethoxy-4-hydroxy-2-methyl-2-[3'R, 4'S-dihydroxy-4'-methylcyclohex -1'R-yl]-(3H)-benzofuran ((+)-24c)

6.35. (+)-7-Carboxyl-4-hydroxy-2-methyl 2-[3′R,4′S-dihydroxy-4′-methylcyclohex-1′R-yl]-(3H)-benzofuran ((+)-24a)

6.36. Complement Inhibition 6.36.1. Demonstration of Inhibition of C3a and C5a Production 6.36.2. Demonstration of Inhibition of Complement-Mediated Hemolysis 6.37. Immunosuppressive Activities 6.37.1. Demonstration of Inhibition of Natural Killer Activity 6.37.2. Demonstration of Inhibition of Proliferation of Peripheral Blood Lymphocytes 6.37.3. Demonstration of Inhibition of Cell Surface Interleukin-2 Receptor Expression 6.37.4. Lack of Inhibition of CHO Cell Proliferation

1. FIELD OF THE INVENTION

The present invention relates to compounds which inhibit complement and/or possess immunosuppressive activity. In particular, the compounds of the present invention, and the pharmaceutically acceptable salts thereof, selectively inhibit complement at the C5 step of complement activation. The compounds of the invention are substituted dihydrobenzofurans, spirobenzofuran-2(3H)cycloalkanes, and their open chain intermediates which exhibit such inhibitory activities. The invention also relates to the use of these compounds for therapy of immune and/or inflammatory disorders.

2. Background of the Invention

2.1. The Complement System

The complement system is a group of proteins that constitutes about 10 percent of the globulins in the normal serum of humans (Hood, L. E. et al. 1984, Immunology, 2d Edition, The Benjamin/Cummings Publishing Co., Menlo Park, Calif., p. 339). Complement (C) plays an important role in the mediation of immune and allergic reactions (Rapp, H. J. and Borsos, T., 1970, Molecular Basis of Complement Action, Appleton-Century-Crofts (Meredith), New York). The activation of C components leads to the generation of a group of factors, including chemotactic peptides that mediate the inflammation associated with complement-dependent diseases. The sequential activation of the complement cascade may occur via the classical pathway involving antigen-antibody complexes, or by an alternative pathway which involves the recognition of certain cell wall polysaccharides. The activities mediated by activated complement proteins include lysis of target cells, chemotaxis, opsonization, stimulation of vascular and other smooth muscle cells, degranulation of mast cells, increased permeability of small blood vessels, directed migration of leukocytes, and activation of B lymphocytes, macrophages and neutrophils (Eisen, H. N., 1974, Immunology, Harper & Row, Publishers, Inc., Hagerstown, Md., p. 512).

During proteolytic cascade steps, biologically active peptide fragments, the anaphylatoxins C3a, C4a, and C5a (See WHO Scientific Group, *WHO Tech. Rep. Ser.* 1977, 606, 5 and references cited therein), are released from the third (C3), fourth (C4), and fifth (C5) native complement components (Hugli, T. E. *CRC Crit. Rev. Immunol.* 1981, 1, 321; Bult, H. and Herman, A. G. *Agents Actions* 1983, 13, 405). The C5a fragment, a cationic peptide derived from the first 74 amino acids of the amino-terminus of the C5 alpha subunit (Tack, B. F. et al. *Biochemistry* 1979, 18, 1490), is of particular pathological relevance. Regulation of C5a activity is by the endogenous plasma enzyme carboxypeptidase N (E.C. 3.4.12.7), which rapidly removes the carboxy-terminal arginine from C5a, producing the less potent but still active C5a des Arg. Reported effects of C3a and C5a upon specific immune responses are listed in Table I.

TABLE I

EFFECTS OF COMPLEMENT COMPONENTS C3a AND C5a ON SPECIFIC IMMUNE RESPONSES

| Immune Response | C3a | C5a/C5a des Arg |
|---|---|---|
| Specific antibody production in response to: Sheep red blood cells | Suppression | Enhancement |
| Polyclonal antibody production in response to: Fc antibody fragment | Suppression | Enhancement |
| T cell proliferation in response to: | | |
| Tetanous toxoid | Suppression | Enhancement |
| Mixed lymphocyte reaction | No effect | Enhancement |
| T cell-mediated cytotoxicity | Suppression | Enhancement |

Among the wide variety of biological activities exhibited by C5a are contraction of smooth muscle (Wissler, J. H. *Eur. J. Immunol.* 1972, 2, 73), degranulation of mast cells (Johnson, A. R. et al. *Immunol.* 1975, 28, 1067), secretion of azurophilic granular enzymes from polymorpho-nuclear neutrophils (PMN) (Webster, R. O. et al. *Immunopharmacol.* 1980, 2, 201), and the chemotaxis of PMN (Wissler, J. H. *Eur. J. Immunol.* 1972, 2, 73; Becker, E. L. *Trends Pharmacol. Sci.* 1983, 4, 223) (Table II).

TABLE II

BIOLOGICAL EFFECTS OF C5a

| | |
|---|---|
| I. | Stimulation of neutrophil functions involved in inflamation |
| | A. chemotaxis |
| | B. chemokinesis |
| | C. aggregation |
| | D. lysosomal enzyme release |
| | E. generation of toxic oxygen products |
| II. | Smooth muscle effects |
| | A. stomach smooth muscle contraction |
| | B. vasodilation |
| III. | Promotion of histamine release |
| | A. mast cells |
| | B. basophils |
| IV. | Immunoregulatory effects |

The active chemotactic factor in vivo is considered to be C5a des Arg (Becker, E. L. *Trends Pharmacol. Sci.* 1983, 4, 223).

The C5a or C5a des Arg fragments have been implicated in the infiltration of PMN (the chemotactic effect) in rheumatoid arthritis, certain forms of glomerulonephritis, experimental vasculitides such as the Arthus reaction, the acute pneumonitis produced by the instillation of chemotactic factors into the lungs of experimental animals with resulting release of leukotrienes C-4 and D-4 ($LTC_4$ and $LTD_4$), etc. In addition, the interactions between C5a and neutrophils have been considered to underlie tissue damage in several clinical situations. For instance, there exists a growing body of evidence for the role of oxygen-derived free radicals in mediating myocardial tissue injury during myocardial ischemia and, in particular, during the phase of myocardial reoxygenation and reperfusion. Among a number of possible sources of these radicals, the polymorphonuclear neutrophil has been the focus of primary attention. Studies have documented that neutrophil depletion or suppression of neutrophil function results in a significant salvage of myocardial tissue that is subjected to a period of regional ischemia followed by reperfusion (Simpson, P. J. and Lucchesi, B. R. *J. Lab. Clin. Med.* 1987, 110(1), 13–30). Neutrophil depletion in dogs resulted in significantly smaller myocardial infarcts after 90 minute occlusion with 24 hour reperfusion (Jolly, S. R. et al. *Am. Heart J.* 1986, 112, 682–690).

One study documented the activation of complement and generation of oxygen-derived free radicals during cardiopulmonary bypass. The administration of protamine during cardiopulmonary bypass further activated-complement (Cavarocchi, N. C. et al. *Circulation* 1986, 74, 130–133; Kirklen, J. K. et al. *J. Thorac. Cardiovasc. Surg.* 1983, 86, 845–857). Also, recombinant tissue plasminogen activator (r-TPA), which in recent clinical trials has been found to be an effective thrombolytic agent in patients with acute myocardial infarction, was shown to activate complement. A striking increase in the level of C4a, C3a, and C5a was found in patients receiving r-TPA as compared to the level of these complement peptides before administration of the drug (Bennett, W. R. et al. *J. Am. Coll. Cardiol.* 1987, 10(3), 627–632).

Schafer and co-workers were able to positively identify the deposition of terminal C5b-9 complement complex in myocardial cells located within zones of infarction in human tissue (*J. Immunol.* 1986, 137(6), 1945–1949). Likewise, the selective accumulation of the first component of complement and leukocytes in ischemic canine heart muscle has been found (Rosen, R. D. et al. *Circ. Research*, 1985, 57, 119–230). In one study, the depletion of complement was found to increase the blood flow in ischemic canine myocardium. This increased blood flow was found, in turn, to increase the supply and utilization of oxygen in complement depleted animals versus control animals (Grover, G. J. and Weiss, H. R. *Basic Res. Cardiol.* 1987 82(1), 57–65).

Complement activation is also believed to initiate adult respiratory distress syndrome (ARDS). This syndrome, also known as adult respiratory failure, shock lung, diffuse alveolar damage, or traumatic wet lungs, is characterized clinically by the rapid onset of severe life-threatening respiratory insufficiency that is refractory to oxygen therapy. (Miescher, P. A. and Muller-Eberhard, H. J., eds., 1976, Text Book of Immunopathology, 2d Ed., Vols. I and II, Grune and Stratton, New York; Sandberg, A. L., 1981, in Cellular Functions in Immunity and Inflammation, Oppenheim, J. J. et al., eds., Elsevier/North Holland, N.Y., p. 373; Conrow, R. B. et al. *J. Med. Chem.* 1980, 23, 242; Regal, J. F.; and Pickering, R. H. *Int. J. Immunopharmacol.* 1983, 5, 71; Jacobs, H. S. *Arch. Pathol. Lab. Med.* 1980, 104, 617). Some of the clinical implications of C5a release are listed in Table III.

TABLE III

| CLINICAL IMPLICATIONS OF C5a RELEASE |
|---|
| Rheumatoid Arthritis |
| Acute Gouty Arthritis |
| Acute Immunological Arthritis |
| Pulmonary Disorders |
| Adult Respiratory Distress Syndrome |
| Pulmonary Dysfunction - Hemodialysis |
| Chronic Progressive Pulmonary Dis-Cystic Fibrosis |
| Byssinosis |
| Asbestos-Induced Inflammation |
| Inflammation of Systemic Lupus Erythematosis |
| Inflammation of Glomerulonephritis |

TABLE III-continued

| CLINICAL IMPLICATIONS OF C5a RELEASE |
|---|
| Purtscher's Retinopathy |
| Hemorrhagic Pancreatitis |
| Renal Cortical Necrosis |
| Primary Biliary Cirrhosis Inflammation |
| Nephropathology |
| Cranial Nerve Damage in Meningitis |
| Tumor Cell Metastasis |
| Extended Tissue Destruction in Myocardial Infarction |
| Extended Tissue Destruction in Burns |

2.2. Cell-mediated Immune Responses

A variety of immune responses independent of the complement system are known to be mediated by specifically reactive lymphocytes. These responses may give rise to autoimmune diseases, hypersensitivity, or simply allergic reactions. Some examples of these responses include delayed-type hypersensitivity, allograft rejection, graft versus host disease, drug allergies, or resistance to infection. Autoimmune disorders may include atrophic gastritis, thyroiditis, allergic encephalomyelitis, gastric mucosa, thyrotoxicosis, autoimmune hemolytic anemia, and sympathetic ophthalmia (Eisen, H. N., 1979, Immunology, Harper and Row, Hagerstown, Md., pp. 557–595).

2.3. Compounds which Inhibit Complement

Many chemicals have been reported to diminish complement-mediated activity. Such compounds include: amino acids (Takada, Y. et al. *Immunology* 1978, 34, 509); phosphonate esters (Becker, L. *Biochim. Biophys. Acta* 1967, 147, 289); polyanionic substances (Conrow, R. B. et al. *J. Med. Chem.* 1980, 23, 242); sulfonyl fluorides (Hansch, C.; Yoshimoto, M. *J. Med. Chem.* 1974, 17, 1160, and references cited therein) ;polynucleotides (DeClercq, P. F. et al. *Biochem. Biophys. Res. Commun.* 1975, 67, 255); pimaric acids (Glovsky, M. M. et al. *J. Immunol.* 1969, 102, 1); porphines (Lapidus, M. and Tomasco, J. *Immunopharmacol.* 1981, 3, 137); several antiinflammatories (Burge, J. J. et al. *J. Immunol.* 1978, 120, 1625); phenols (Muller-Eberhard, H. J., 1978, in Molecular Basis of Biological Degradative Processes, Berlin, R. D. et al., eds. Academic Press, New York, p. 65); and benzamidines (Vogt, W. et al. *Immunology* 1979, 36, 138). Some of these agents express their activity by general inhibition of proteases and esterases. Others are not specific to any particular intermediate step in the complement pathway,, but, rather, inhibit more than one step of complement activation. Examples of the latter compounds include the benzamidines, which block C1, C4 and C5 utilization (Vogt, W. et al. *Immunol.* 1979, 36, 138).

2.4. Spirobenzofuran-2(3H)-Cycloalkanes and K-76

K-76 is a recently described fungal metabolite from *Stachybotrys complementi* nov. sp. K-76. Metabolite K-76 has a drimane skeleton combined with a benzene ring attached through a spirofuran, and has been determined ,as 6,7,-diformyl-3',4',4a',5',6',7',8',8a'-octahydro-4,6',7'-trihydroxy-2',5',5',8a'-tetramethyl spiro [1'(2'H) -naphthalene-2(3H)-benzofuran] (Kaise, H. et al. *J. Chem. Soc. Chem. Commun.* 1979, 726). The monocarboxylic acid derivative, K-76 COOH, is obtained when K-76 is selectively oxidized by silver oxide (Corey, E. J. and Das, J. *J. Amer. Chem. Soc.* 1982, 104, 5551).

Both K-76 and K-76 COOH have been shown to inhibit complement mainly at the C5 step (Hong, K. et al. *J. Immunol.* 1979, 122, 2418; Miyazaki, W. et al.

*Microbiol. Immunol.* 1980, 24, 1091). In a classical hemolytic reaction system, hemolysis of sensitized sheep erythrocytes by guinea pig serum was reduced 50% by K-76 at $7.45 \times 10^{-5}$M, or K-76 COONa at $3.41 \times 10^{-4}$M (Hong, K. et al. *J. Immunol.* 1979, 122, 2418; Miyazaki, W. et al. *Microbiol. Immunol.* 1980, 24, 1091). Similar results were observed in a hemolytic reaction system via the alternative pathway of complement activation.

Both K-76 and K-76 COOH prevented the generation of a chemotactic factor from normal human complement (Bumpers, H. and Baum, J. *J. Lab. Clin. Med.* 1983, 102, 421). K-76 has been shown to reduce the amount of protein excreted in the urine of rats with nephrotoxic glomerulonephritis (Iida, H., et al., *Clin. Exp. Immunol.* 1987, 67, 130–134), and is reported to greatly increase the survival of mice with a spontaneous systemic lupus erythematosis-like disease and to suppress Forssman shock in guinea pigs and mice (Miyazaki, W. et al. *Microbiol. Immunol.* 1980, 24, 1091). At high concentrations of K-76 or K-76 COOH, some inhibition of the reactions of C2, C3, C6, C7, and C9 with their respective preceding intermediaries is exhibited. However, both compounds' inhibitory action is mainly on the C5 step. The compounds strongly inhibit the generation in vitro of EACl, 4b,2a,3b,5b (sensitized sheep erythrocytes carrying the indicated complement components) from C5 and EACl,4b,2a,3b; accelerate the decay of any EACl,4b,2a,3b,5b present; and block generation of the chemotactic peptides (Hong, K. et al. *J. Immunol.* 1981, 127, 109; Ramm, L. E., et al. *Mol. Immunol.* 1983, 20, 155).

K-76 COOH is also reported to be an anti-hepatitic agent (West German Patent Application, Publication No. 3,031,788, published Mar. 12, 1981, by Shinohara, M. et al.), and possesses the ability to inhibit antibody-dependent cell-mediated cytotoxicity and natural killer lytic activity (Hudig, D. et al. *J. Immunol.* 1984, 133, 408–413). K-76 or K-76 COOH has also been reported to inhibit the C3b inactivator system of complement (Hong, K. et al. *J. Immunol.* 1981, 127, 104–108). Semisynthetic derivatives of K-76 have been patented as anti-allergy, anti-tumor, and anti-nephritic agents (Belgium Patent No. 867,095, published Nov. 16, 1978, by Shinohara, M. et al.). The isolation of K-76, its uses in the treatment of autoimmune diseases, and the preparation of its derivatives have been described in a number of patents (See Japanese Patent Applications (Kokai), Publication Nos. 54 092680 (published Jul. 23, 1979), 54 106458 (published Aug. 21, 1979), 57 083281 (published May 25, 1982), , by Shinohara, M. et al.; Japanese Patent (Kokoku) No. 85 030289 (published Mar. 20, 1979)).

A number of compounds which contain the substructure of a spirobenzofuran-2(3H)-cycloalkane are known. These compounds include griseofulvin (Weinberg, E. D., 1981, in Principles of Medicinal Chemistry, 2d Ed., Foye, W. O., ed., Lea & Febiger, Philadelphia, Pa., p. 813), isopannarin (Djura, P. and Sargent, M. V. *Aust. J. Chem.* 1983, 36, 1057), metabolites of *Siphonodictyon coralli-phagum* (Sullivan, B., et al. Tetrahedron 1981, 37, 979), and the fungal metabolite K-76 (Kaise, H. et al. *J. Chem. Soc. Chem. Comm.* 1979, 727).

The general synthetic methodology utilized for the synthesis of the compounds of the present invention involves regioselective aromatic lithiation reactions. Numerous oxygen-containing heterocycles have been made using regioselective aromatic lithiation reactions, but few preparations of dihydrobenzo[b]furans have been described (Narasimhan, N. S. and Mali, R. S. *Synthesis* 1983, 957). Two reported syntheses of K-76 itself (Corey, E. J. and Das, J. J. *J. Am. Chem. Soc.* 1982, 104, 5551; McMurray, J. E. et al. *Am. Chem. Soc.* 1985, 107, 2712) utilize metalation techniques in the coupling of the terpenoid portion to the aromatic moiety, but neither provide sufficient flexibility to allow for analog preparation via subsequent elaboration of the aromatic ring.

3. Summary of the Invention

The present invention is directed to compounds which suppress immune responses and/or selectively inhibit complement. In specific embodiments, such compounds interrupt the proteolytic processing of C5 to bioactive components, blocking the release of C5a. The compounds of the present invention also exhibit immunosuppressive activities, such as for example, the ability to inhibit natural killer activity, lymphocyte proliferation, and T cell activation. The compounds of the present invention have therapeutic utility in the amelioration of disease and disorders mediated by complement and/or immune activity. In specific embodiments, they may be used for the treatment of autoimmune disease or the many diseases associated with the "inappropriate" activation of the complement system.

In one embodiment of the present invention, compounds are provided which have selectivity in inhibition of C5a release. In particular, such compounds can have utility in limiting the extent of trauma-induced tissue destruction, in the prevention and/or treatment of adult respiratory distress syndrome and damage induced by ischemic heart conditions.

In other specific embodiments, compounds of the invention which exhibit immunosuppressive activity can be used in the prevention and/or treatment of autoimmune disease or the rejection of transplanted organs and/or tissues.

The present invention is also directed to pharmaceutical compositions comprising such compounds or the salts thereof.

3.1. Definitions

As used herein, the following abbreviations and terms shall have the meanings indicated:

| | |
|---|---|
| n-BuLi = | n-butyllithium |
| t-BuSLi = | lithium tert-butylthiolate |
| C = | complement; carbon |
| CHO = | Chinese hamster ovary |
| CPM = | counts per minute |
| Et$_2$O = | diethyl ether |
| HMPA = | hexamethylphosphoric triamide |
| IgG = | immunoglobulin G |
| IR = | infrared |
| K-76 COOH = | the monocarboxylic acid derivative of K-76 |
| K-76 COONa = | the sodium salt of the monocarboxylic acid derivative of K-76 |
| LAH = | lithium aluminum hydride |
| MOM = | methoxymethyl group |
| NK = | natural killer |
| NMR = | nuclear magnetic resonance |
| $^i$PROH = | isopropanol |
| PBL = | peripheral blood lymphocyte(s) |
| PCC = | pyridinium chlordchromate |
| PRA = | phytohemagglutinin |
| PMN = | polymorphonuclear cells |
| RLi = | alkyllithium |
| THF = | tetrahydrofuran |
| TLC = | thin layer chromatography |
| TMEDA = | N,N,N',N'-tetramethylethylenediamine |
| TMS = | tetramethylsilane |

Unless otherwise stated or indicated, the term "alkyl" as used herein refers to methyl, ethyl, and n-propyl, isopropyl, n-butyl, isobutyl, sec-butyl, or tert-butyl groups. The term "alkanol" denotes a compound derived from coupling an alkyl group and hydroxyl radical. Similarly, the term "alkoxy" refers to methoxy, ethoxy, n-propyloxy, isopropyloxy, n-, iso-, sec-, and tert-butoxy groups. The term "lower" refers to the numerical range of 1 to 4 carbon atoms and includes linear or branched skeletons.

Unless otherwise stated or indicated, the term "halogen" as used herein includes fluorine, chlorine, bromine, and iodine.

Unless otherwise stated or indicated, a given structure, formula, or nomenclature for the substituted dihydrobenzofuran analogs of this invention shall subsume all stereoisomers thereof.

Unless otherwise stated or indicated, a reference made to a final compound of the invention which is a carboxylic acid, is also meant to include the salt form of such carboxylic acid such as alkali and alkaline-earth metal salts obtained therefrom.

4. BRIEF DESCRIPTION OF THE FIGURES

FIG. 1 illustrates the infrared spectrum of compound 11a. The spectrum is presented for the compound pelletized in potassium bromide.

Figure 2:
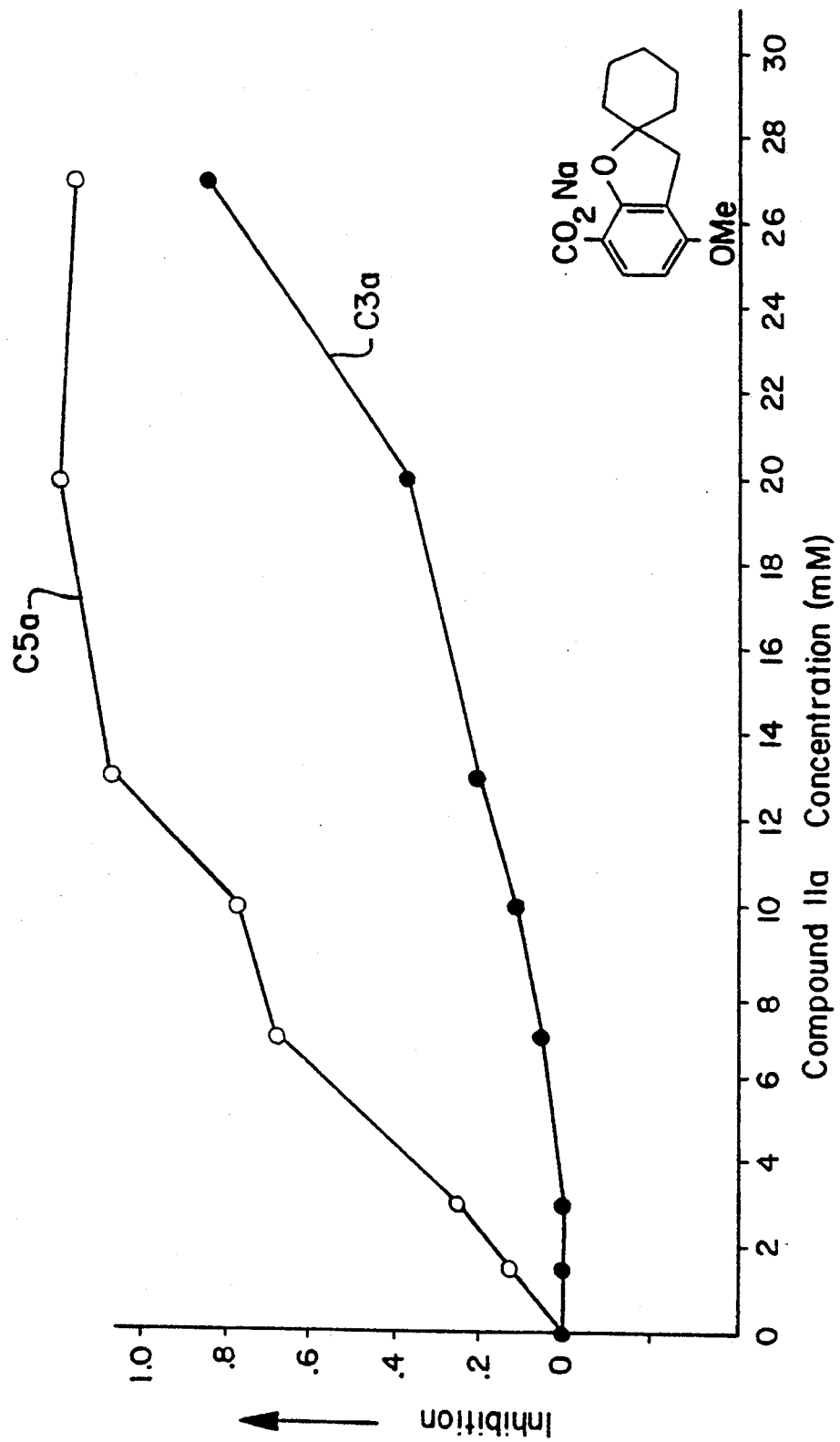

FIG. 2 demonstrates the inhibition of complement peptide C5a or C3a production by compound 11a. The fraction inhibition (as defined in Section 6.34, infra) of C5a and C3a production is shown as a function of compound 11a concentration.

Figure 3:
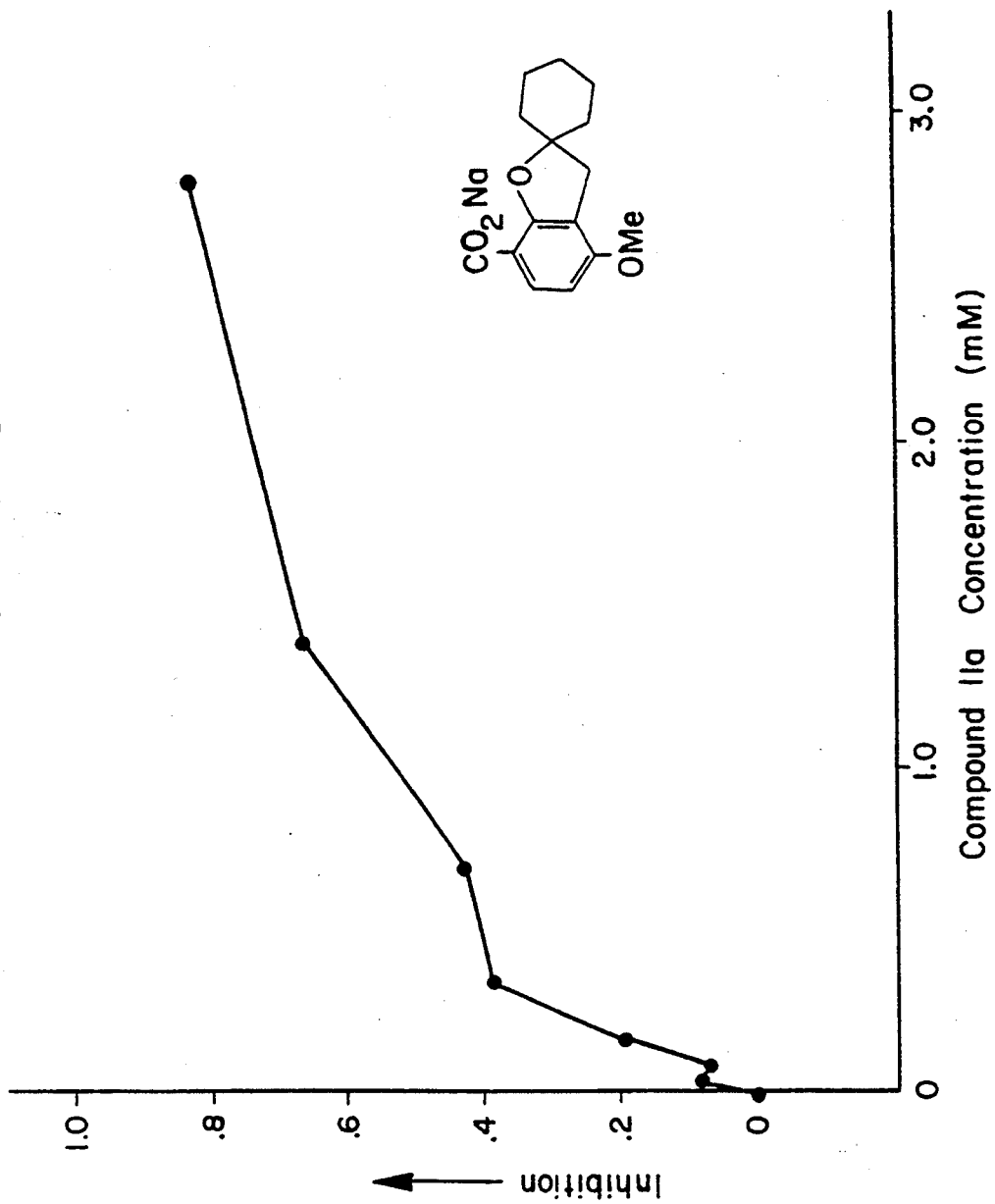

FIG. 3 demonstrates the inhibition of complement-mediated hemolysis by compound 11a. Inhibition of complement-mediated hemolysis, assayed as described in Section 6.36.2 infra, is shown as a function of compound 11a concentration.

Figure 4:
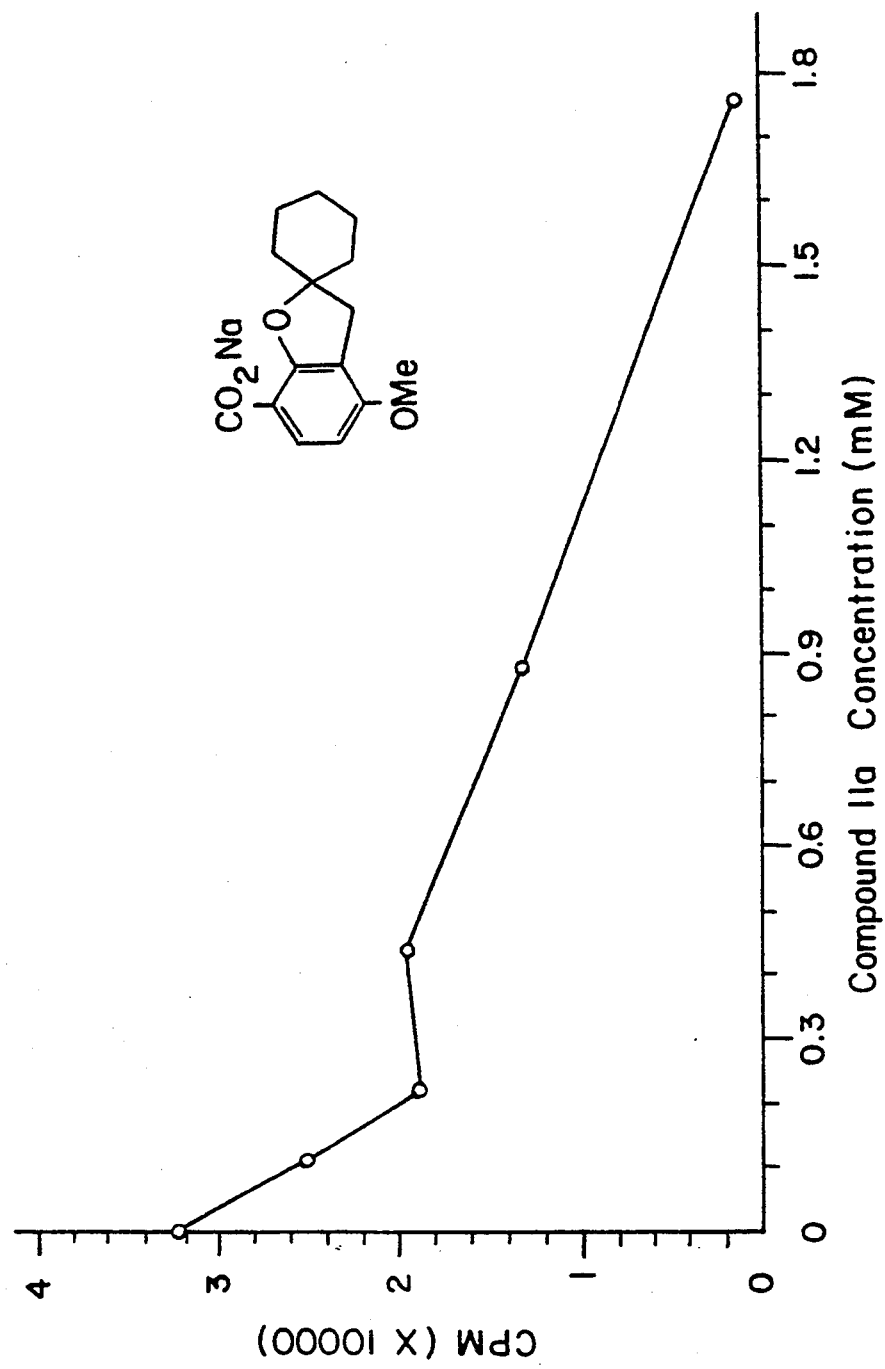

FIG. 4 demonstrates the inhibition of proliferation of peripheral blood lymphocytes (PBL) by compound 11a. Thymidine incorporation by PHA-stimulated PBL is shown as a function of compound 11a concentration.

Figure 5:
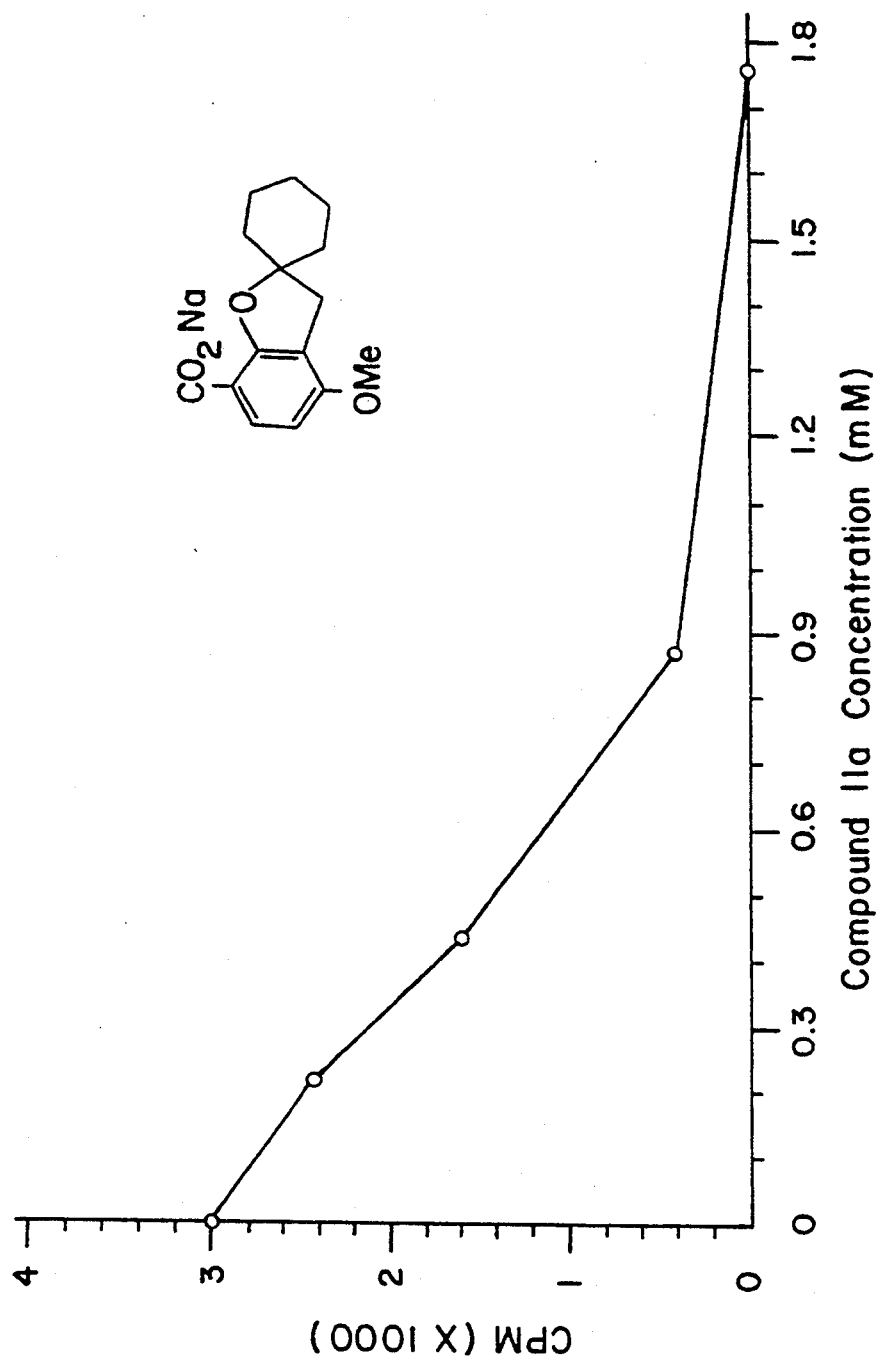

FIG. 5 demonstrates the inhibition of proliferation of PBL by compound 11a. Thymidine incorporation by anti-CD3 antibody-stimulated PBL is shown as a function of compound 11a concentration.

Figure 6:
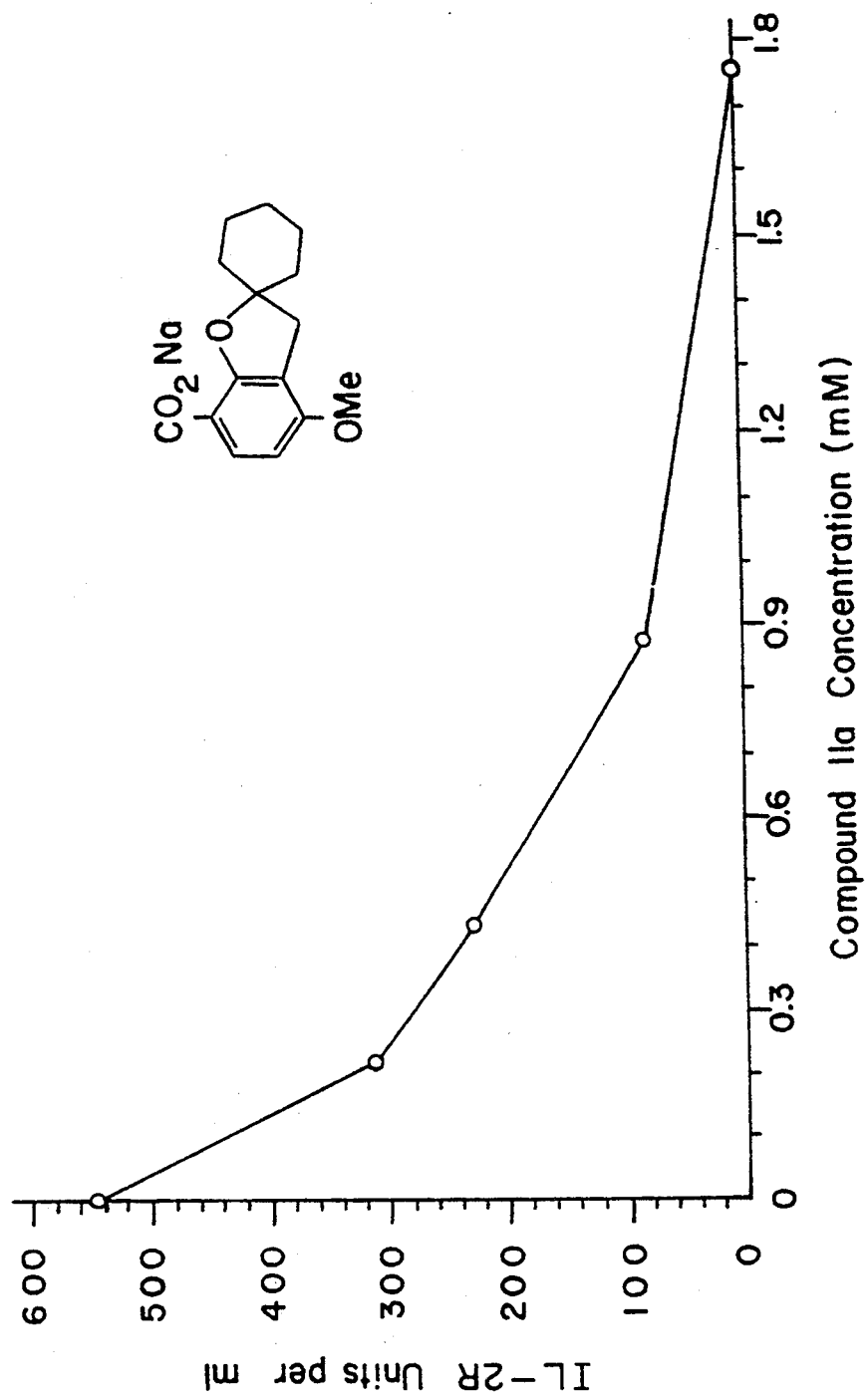

FIG. 6 demonstrates the inhibition of interleukin-2 receptor (IL-2R) release from PBL by compound 11a. The level of IL-2R in the supernatant of PBL cultures stimulated with anti-CD3 antibody, in the presence of compound 11a, was measured by use of an enzyme-linked immunosorbent assay, and is shown as a function of compound 11a concentration.

Figure 7:
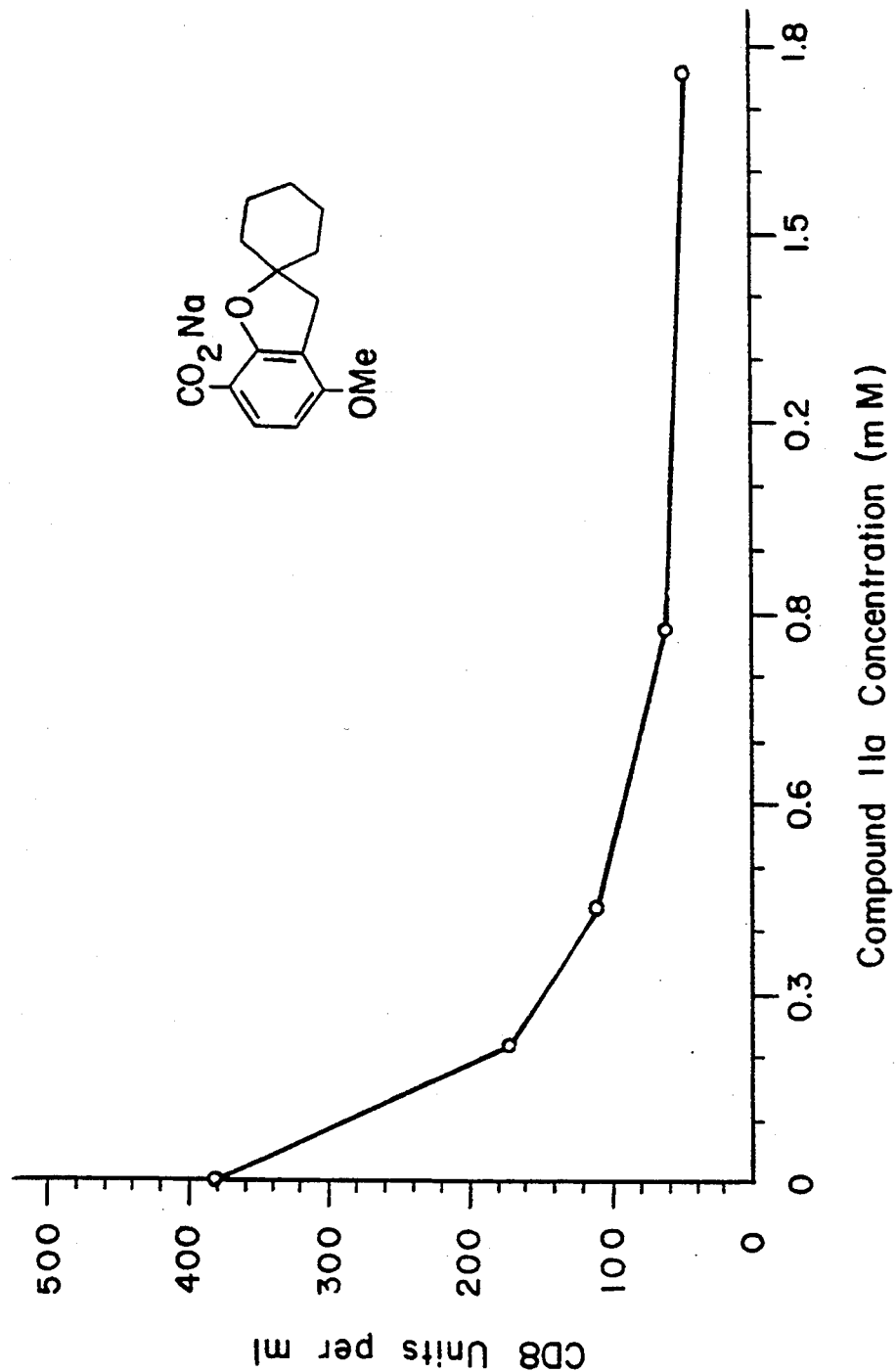

FIG. 7 shows the inhibition of CD8 protein release from PBL by compound 11a. The level of CD8 in the supernatant of PBL cultures stimulated with anti-CD8 antibody, in the presence of compound 11a, was measured by use of an enzyme-linked immunosorbent assay, and is shown as a function of compound 11a concentration.

5. DETAILED DESCRIPTION OF THE INVENTION

The present invention relates to compounds which inhibit complement and/or possess immunosuppressive activity. The compounds of the invention contain an aromatic ring and are substituted dihydrobenzofurans, spirobenzofuran-2(3H)-cycloalkanes, and their open chain intermediates. In particular, such compounds can be partial analogs of the fungal metabolite K-76.

The complement inhibitors of the invention inhibit C5 activation, that is, the proteolytic generation of bioactive complement fragments C5a and C5b from C5. Such compounds have value in the treatment or prevention of diseases or disorders associated with undesirable or inappropriate activation of the complement system. In specific embodiments, the compounds of the invention can be used in the treatment of inflammatory disorders. They may also be used for the treatment of cardiovascular disease.

The present invention also relates to compounds which possess immunosuppressive activity. In particular, such compounds inhibit immune responses. In specific embodiments, the compounds of the invention can inhibit the killing activity of mononuclear cells, lymphocyte proliferation and/or activation. The immunosuppressive compounds of the invention can be valuable in the treatment of various immune disorders.

Furthermore, the compounds of the invention may possess one or more of the K-76-like activities described Supra in Section 2.4 and in the references cited therein.

The compounds of the present invention, and the intermediates and methods used in their preparation, are described in detail below.

5.1. Compounds which Inhibit Complement and/or Suppress Immune Activity

The present invention relates to compounds which inhibit complement and/or suppress immune activity. The compounds of the invention comprise substituted dihydrobenzofurans of the general formula 3 and substituted spirobenzofuran-2(3H)-cycloalkanes of the general formula 4. The groups represented by R and $R_1$–$R_6$ include hydrogen and linear or branched lower alkyl groups having 1 to 4 carbon atoms as defined previously in Section 3.1, supra. In addition, $R_1$–$R_4$ may each independently represent halogen,

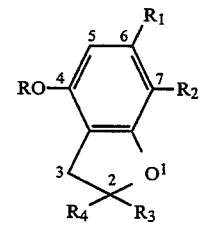

3

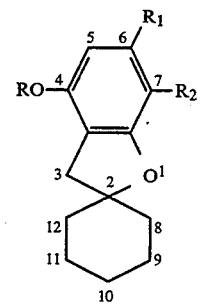

4 amino, amidic, hydroxyl, hydroxyalkyl, alkyloxy, nitro, formyl, acetal, carboxyl, trifluoroacetyl, N-substituted lower alkyl carboxamide, substituted vinyl of 2–10 carbon atoms, or alkylidene group of 2–20 carbon atoms.

In a specific embodiment of the present invention, $R_1$ is a hydrogen atom when $R_2$ is a carboxyl group, a formyl group, a hydroxymethyl group, an N-(lower alkyl) carboxamide group, a trifluoroacctyl group, a carbalkoxy group, a halide group, a substituted vinyl group of 2–10 carbon atoms, or a alkylidene group of 2–20 carbon atoms. Further, $R_2$ is a hydrogen atom when $R_1$ is a carboxyl group, a formyl group, a hydroxymethyl group, an N-(lower alkyl) carboxamide group, a tfifluoroacetyl group, a carbalkoxy group, a halide group, a substituted vinyl group of 2–10 carbon atoms, or an alkylidene group of 2–20 carbon atoms.

Other groups which may be represented independently by $R_3$ and $R_4$ include hydrocarbons of 4 to 24 carbon atoms which may be of medium-length, long-chain, linear, branched, cyclic, saturated, unsaturated, unsubstituted, or heteroatom substituted. Moreover, $R_3$, $R_4$, and the carbon atom to which they are attached may form a cyclic hydrocarbon group of 5–24 carbon atoms which may include a five-, six-, or seven-membered saturated or unsaturated ring comprised exclusively of carbon and hydrogen, or in combination with a hetero-atom. The ring may be unsubstituted or may contain extra-cyclic hetero-atom or hydrocarbon substituents.

This invention also relates to synthetic open chain intermediate compounds of the general formula 5 wherein R, $R_1$, and $R_2$ are defined as above for formulae 3 and 4. In addition, $R_5$ represents hydrogen, lower alkyl groups, or suitable hydroxyl protecting groups such as methoxymethyl, tetrahydropyranyl, 2-methoxypropyl, 2-methoxyehoxymethyl, triarylmethyl, benzyl, methylthiomethyl, or tertbutyldimethylsilyl group. The $R_6$ group encompasses chemical groups represented by $R_1$–$R_4$ as defined above for formulae 3 and 4 as well as substituent cyclohexenylmethyl (5a), limonenyl (5b), and carvone-derived diol acetonide (5c) groups. Other compounds may also be derived from

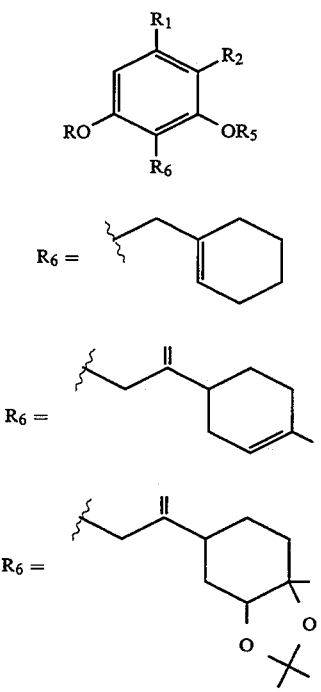

intermediates 5 and 5a–c, which are, in turn, converted to the products of general formulae 3 or 4 as discussed in the following sections.

Table V lists representative compounds which comprise the general formula 4 of the present invention; this list is not intended to be comprehensive.

TABLE V

COMPLEMENT INHIBITORS OF THE PRESENT INVENTION[a]

| | |
|---|---|
| R = | —H, —CH₃ |
| R₁ or R₂ = | —H, —CHO, —COOH, —CH₂OH, —CONHCH₃, —CONH$^t$Bu, —COCF₃, —X (where X = halogen), —CH=CHCOOH |

[a]Substituents on the spirocyclohexane ring may also be present; e.g., 10-isopropenyl.

The substituted dihydrobenzofuran and spirobenzofuran-2(3H)-cyclohexane compounds of the present invention of the general formulae 3, 4, the synthetic intermediates of the general formula 5, and the salts thereof exhibit complement inhibition, as manifested by inhibition of complement-mediated C5a production and/or inhibition of complement-mediated hemolysis. The complement-inhibitory properties of the compounds of the invention can be evaluated by modification of known techniques, e.g., the assay described in Section 6.3 6.1, infra.

Treatment of the compounds of the present invention with appropriate betsic reagents provides pharmaceutically acceptable salts thereof.

5.2. Synthetic Processes

Processes are provided which comprise chemical steps for the synthesis of the compounds of the invention.

The processes of the invention are diagrammed in detail in Scheme 1 (See infra Section 5.2.2). The synthetic scheme depicted in Scheme 1 provides a shorter and more flexible route than one based on the syntheses of K-76 (Corey and Das *J. Am. Chem. Soc.* 1982, 104, 5551; McMurray et al. *J. Am. Chem. Soc.* 1985, 107, 2712). Retrosynthetic evaluation of all the final compounds produced according to Scheme 1 ultimately results in two fragments; an aliphatic and an aromatic portion. These two portions can be joined by using regioselective ortho-lithiation and subsequent alkylation. Two different strategies can then be employed for the production of the final compound of the-invention: initial cyclization followed by aromatic functionalization or vice versa.

5.2.1. Preparation of Compounds of General Formula 5

The intermediates of the general formula 5 of the invention can be prepared by various methods depending on the types of substituents present therein.

The aliphatic substituent, $R_6$, of compounds of the general formula 5 are derived from suitable alkylating agents. For example, 1-bromomethylcyclohexene, 6a, can be used as the starting material for the preparation of compound 5a. Compound 6a can in turn be prepared from cycolhexanone or directly from alkyl cyclohexenecarboxylate, according to a known process (Wheeler, O. H. and Lerner, I. *J. Am. Chem. Soc.* 1956, 78, 63; Adams, R. and Thai, A. F. *Org. Synth.* 1932, 1, 270; Lythgoe, B. et al. *J. Chem. Soc.* 1956, 406). In a particular example, cyclohexanone is converted to its cyanohydrin, then dehydrated to the cyanoalkene, followed by alcoholysis to an alkyl cycloalkenecarboxylate. Lithium aluminum hydride reduction of the ester followed by halogenation with phosphorus trihalide provides compound 6a.

Limonenyl chloride, 6b, is obtained readily from limonenyl alcohol by the action of triphenylphosphine in excess halogenated solvent. This convertion provides optically active allylic halide from optically active limonenyl alcohol. A procedure analagous to that developed by Crawford and co-workers (J. Am. Chem. Soc. 1972, 94, 4298) is used to prepare optically active alcohol by the sequential lithiation of commercially available homochiral limonene, oxygenation, and reduction of the resultant hydroperoxide with aqueous sodium sulfite.

A third halointermediate, 6c, is derived from a multistep sequence starting from optically active R-(—)-or S-(+)-carvone. The steps of the synthesis involve reduction of the α,β-unsaturated ketone to the allylic alcohol, epoxidation, reduction to the diol, acetonide formation, and treatment of the unsaturated acetonide with calcium hypochlorite to yield the allylic chloride. The coupling reaction is generally carried out immediately after purification of these unstable allylic halides.

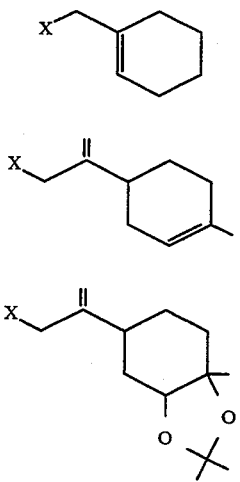

6a

6b

6c

The aromatic segment of the compounds of the general formula 5 is obtained from substituted alkoxyphenols or resorcinols. For example, 3-methoymethoyanisole, 7, is obtained from the reaction of 3-methoxyphenol with chloromethyl methyl ether in a stirred suspension of anhydrous potassium carbonate in acetonitrile (Rall, G. J. H. et al. Tet. Lett. 1976, 1033). Anhydrous conditions and the proper ratio of substrate to solvent are critical to the

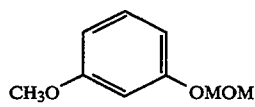

7 success of this reaction. For reactions employing quantities of reagents above 5 grams, a useful alternative procedure uses the pre-formed sodium aryloxide, chloromethyl methyl ether, and dimethylformamide as solvent (.See, Rall, G. J. H. et al. supra).

The group R of formulae 5 and 5a-c should be stable to cleavage under the conditions used to hydrolyze or remove the protecting group $R_5$ and the subsequent cyclization of the resulting free phenol according to steps 3 or 4 of Scheme 1. In addition, $R_5$ is preferably a potentially chelating group which can promote the regioselective orthometalation required to introduce substituents $R_2$ and $R_6$ of formula 5. Compound 7 embodies the preferred protecting groups for resorcinol (R=methyl and $R_5$=methoxymethyl). The methoxymethyl or MOM ethers can be easily removed in the presence of methyl ethers (Narasimhan, N. S. et al. Synthesis 1979, 906), and the ortho directing power of the MOM group has been shown to be greater than that of a methyl ether (Ronald R. C. Tet. Lett. 1975, 3973).

In an alternative embodiment, the commercially-available compound 3,5-dimethoxybenzyl alchol, 8, can be used as the aromatic segment for coupling to the allylic halide (See Scheme 2, infra).

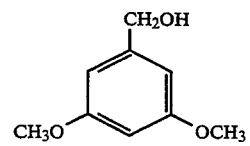

8

The efficacy of the coupling reaction between the metalated aromatic segment and the aliphatic group is greatly influenced by a number of factors including the degree of aggregation of the metalating species, typically an alkyllithium reagent (Gschwend, H. W. and Rodriguez, H. R. Org. React. 1979, 26, 1). The choice of solvent and any additives such as N,N,N'N'-tetramethylethylenediamine (TMEDA) or hexamethylphosphoric triamide (HMPA), in turn, strongly influences this state. Solvent(s), additive(s), temperature, reaction time, and reagent stoichiometries for coupling the respective substrates should be optimized. Suitable solvents include anhydrous aprotic organic solvents such as tetrahydrofuran (THF), diethyl ether ($Et_2O$), dioxane, and diglyme. Surprisingly, we have discovered that dry hexane is a preferred solvent for selective metalation ortho to a chelating group like OMOM and lithioalkoxymethyl (kinetic conditions), while THF/TMEDA solvent mixtures, generally, provide for metalation at the thermodynamic site, between the two inductively electron-withdrawing methoxy groups in 8, for example. In one particular embodiment, n-butyllithium (n-BuLi) in THF/TMEDA or hexane/TMEDA allows for the coupling of aromatic segment 7 with allylic bromide 6a; however, only THF/TMEDA allows coupling of 6a with aromatic segment 8 at the desired 4-position (thermodynamic). When the coupling between 6a and 8 is carried out in hexane, lithiation and coupling occurs in the 2-position of 8 (the kinetically favored position).

The aromatic substrate is dissolved in the solvent such as dry THF and the like. The TMEDA is then added and is preferably approximately equimolar to the amount of alkyllithium used. In a preferred embodiment, the amount of alkyllithium (RLi) slowly added at 0° C. is approximately 1.1 equivalents per equivalent of a compound of the type such as 7 and is approximately 2.2 equivalents per equivalent of a substrate such as 8 that has an additional acidic hydrogen. Moreover, the addition of approximately 1.2 equivalents of a copper salt per equivalent of the lithiated aromatic substrate is preferred to obtain optimum yields from the coupling reaction. Most sources of copper(I) are suitable including cuprous bromide dimethylsulfide, tetrakis (acetonitrile) copper(I) tetrafluoroborate, and the cuprous halides. The use of cuprous iodide is preferred.

Careful control of temperature is important for the success of the aromatic alkylation. While the lithiation is carried out at zero degrees to ambient temperature, the subsequent reactions are carried out at low temperature. In a preferred example, the aryllithium reagent is cooled to −78° C. followed by the addition of the copper(I) salt. The resulting mixture is subsequently stirred at −40° C., a temperature at which the corresponding arylcuprate species can form and is relatively stable. The copper reagent is then recooled to −78° C. prior to the addition of the electrophile. Carrying out the addition at higher temperatures can diminish the yields of coupled products such as 5. It is important that all the manipulations discussed supra be performed in the absence of oxygen and moisture, and are preferably carried out under an inert atmosphere such as dry nitrogen or argon.

The product mixture which is obtained from the coupling reaction can then be worked up by washing several times with a moderately basic aqueous solution, e.g., saturated aqueous sodium bicarbonate (NaHCO$_3$). The organic phase can be dried by shaking with a drying agent such as magnesium sulfate, filtered from any solids, and concentrated under a mild vacuum to provide the crude product. Further purification may then be effected by procedures typically employed in the art (e.g., fractional distillation, fractional crystallization, or chromatographic separation).

5.2.2. Preparation of Compounds of the General Formulae (3 and 4)

Substituted dihydrobenzofuran derivatives of the general formula 3 with substituents OR and R$_1$-R$_4$ as defined supra in Section 5.1 can be obtained by the metalation and subsequent alkylation of coupled intermediates such as those described in the preceding section, followed by hydrolysis of the protecting groups and cyclization of the ene-phenol. This synthetic pathway is illustrated in Scheme 1, infra.

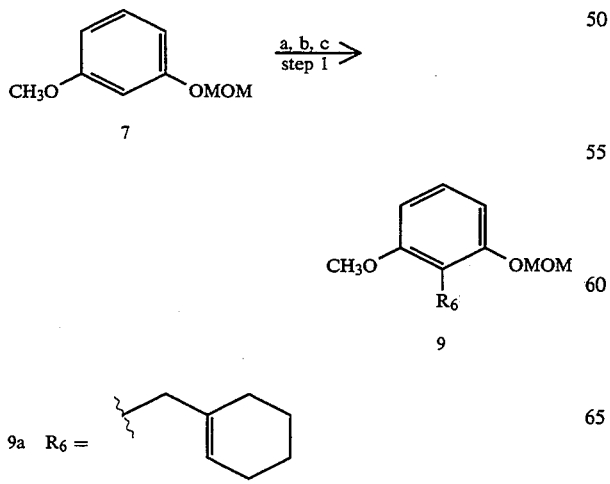

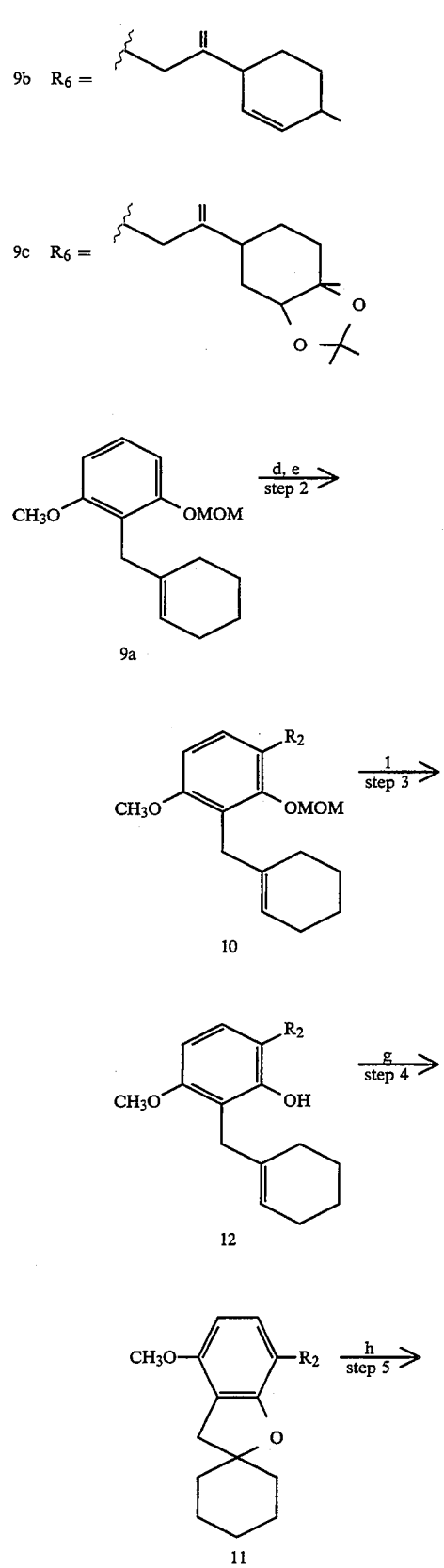

-continued
Scheme 1

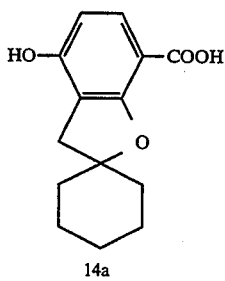

14a
(4, R, R₁ = H, R₂ = COOH)

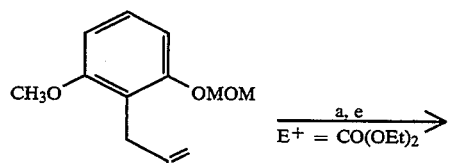

9b

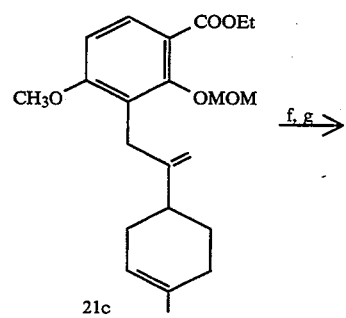

21c

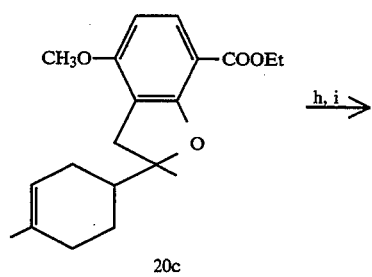

20c

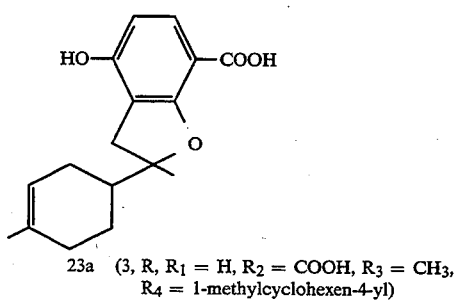

23a (3, R, R₁ = H, R₂ = COOH, R₃ = CH₃, R₄ = 1-methylcyclohexen-4-yl)

-continued
Scheme 1

(a) $^n$BuLi, THF/TMEDA; (b) CuI; (c) R₆X;
(d) $^n$BuLi, Hexana/TMEDA;
(e) E⁺ (R₂); (f) H⁺, $^i$PrOH; (g) Amberlyst resin;
(h) $^t$BuSLi, HMPA; (i) aq. 40% KOH In a preferred embodiment, the protected resorcinol is lithiated and alkylated in step 1 of Scheme 1 using the allylic bromide 6a as the electrophile. The resulting coupled product 9a can then be dissolved in dry hexane and treated dropwise with alkyllithium in the presence of TMEDA (step 2) at 0° C. Cooling the reaction mixture to −78° C. and addition of the desired electrophile introduces the R₂ substituent at this stage.

Generally, the MOM protecting group of intermediates such as 9, with or without the R₂ substituent, may be hydrolyzed by stirring the compound in 5% hydrochloric acid (HCl)/ether mixtures overnight. Deprotection to the free phenol may also be effected by a solvent mixture comprised of 4N HCl/$^i$PrOH, especially for carboxaldehyde containing derivatives, which need to be stirred for several days. The cyclization step can be achieved most conveniently by stirring the substrate in the presence of Amberlyst resin in a non-polar solvent followed by filtration. In this particular process, the resin is washed with fresh solvent, and the filtrates are combined and concentrated to give the desired crude cyclized product in good yield. In the particular case where R₂=—COOH In intermediate 10a (Scheme 1, step 2, E⁺=CO₂), the cyclization of the phenol (steps 3 and 4) can be achieved by stirring with Amberlyst resin in benzene for 24–72 hours at room temperature. Some difficulty is encountered in the cyclization of intermediates with hydroxymethyl substituents (e.g., R₂=—CH₂OH). A different route is preferred for synthesis of cyclized products with this substituent (see below).

As discussed supra, a variety of R₂ substituents may be introduced before the cyclization step. For example, addition of the following electrophiles to the aryllithium species produces the indicated functional group (these examples serve only to illustrate the technique and are not meant to limit the invention): carbon dioxide (carboxyl); ethyl chloroformate or diethyl carbonate (carbethoxy); dimethylformamide (formyl); methylisocyanate (N-methylcarboxamide); tert-butylisocyanate (N-tert-butylcarboxamide); paraformaldehyde (hydroxymethyl); trifluoroacetic anhydride (trifluoroacetyl); bromine (bromide); chlorine (chloride); iodine (iodide); substituted vinyl iodides (substituted vinyl group). Other compounds may, in turn, be obtained by modification of these functional groups by known methods.

The cyclized methyl ether derivatives of the type, 11 can be converted to the free phenols, 14 (Scheme 1, step 5), by known methods. These procedures include but are not limited to treatment of the methyl ether with boron trihalides (McOmie, J. F. W. and West, D. E. Org. Synth. 1973, 5, 412; Grieco, P. A. et al. J. Org. Chem. 1975, 40, 1450), boron trifluoride in the presence of thiols (Fujita, E. et al. Ibid. 1979, 44, 1661; Fujita, E. J. Chem. Soc. Perkin Trans. 1 1976, 2237), trimethylsilyl iodide (Jung, M. E. and Lyster, M. A. Org. Synth. 1980, 59, 35; Vickery, E. J. Org. Chem. 1979, 44, 4444), and lithium tert-butylthiolate salts (t-BuSLi) in hexamethylphosphoric triamide (McMurry, J. E. and Erion, M. D. J. Am. Chem. Soc. 1985, 107, 2712). The use of t-BuSLi is preferred.

Open-chain coupled products such as 9b or 9c (See Scheme 1) give rise to compounds such as 21 or 25, respectively. The latter intermediates, wherein the olefinic bond involved in the cyclization is exocyclic, or other derivatives containing simple unsaturated aliphatic groups, produce dihydrobenzofuran derivatives disubstituted at the 2-position upon deprotection and treatment with Amberlyst ion-exchange resin (See e.g., 20).

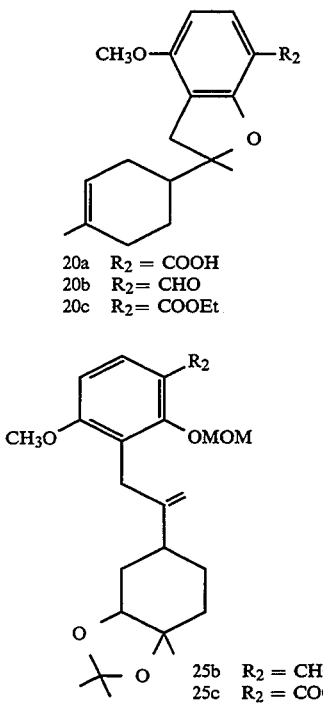

20a  $R_2$ = COOH
20b  $R_2$ = CHO
20c  $R_2$ = COOEt

25b  $R_2$ = CHO
25c  $R_2$ = COOEt

Slightly more complex analogs containing a diol group, such as 24 or 27, infra, can be obtained in this manner.

The use of 3,5-dimethoxybenzyl alcohol, 8, as the starting aromatic component has the advantage of having the $R_1$ substituent already in place. Compound 8 is dissolved in THF and is treated at 0° C. with 2.0 equivalents of n-butyllithium in the presence of TMEDA (2.0 equiv). The benzyl alcohol is lithiated predominantly at the 4-position after about 2 hours. Formation of the arylcuprate at −40° C. and addition of the alkylating agent completes the synthesis. of 13 (Scheme 2, step 1) with a small amount of the isomer 13′ also being formed. Fractional crystallization of the product mixture provides pure 13.

As previously alluded to, cyclization of intermediates with hydroxymethyl substituents can be problematic. In one embodiment, a remedy to this problem involves converting the benzyl alcohol 13c to the formyl compound 13b (See Scheme 2, step 2). This procedure can be accomplished by a Swern oxidation or, more preferably, by using pyridinium chlorochromate in "buffered" methylene chloride (See Examples Section 6.12). One of the symmetrical methyl ethers is then selectively cleaved (step 3) and cyclized in the normal fashion to yield the 6-substituted formyl analog 30b. Oxidation of the formyl group to the carboxylic acid (e.g., 30a or 31a) can be effected by a number of reagents either before or after the cyclization of step 4. Suitable inorganic oxidizing agents include but are not restricted to permanganate salts, manganese oxide, chromic acid, chromate salts, silver oxide, silver nitrate, nickel peroxide, and cerium salts such as cerium sulfate, cerium oxide, and cerium perchlorate. Silver oxide is preferred. The benzyl alcohol, 30c (4, R=CH$_3$, R$_1$=CH$_2$OH, and R$_2$=H), is obtained by reduction of 30b using, for example, such

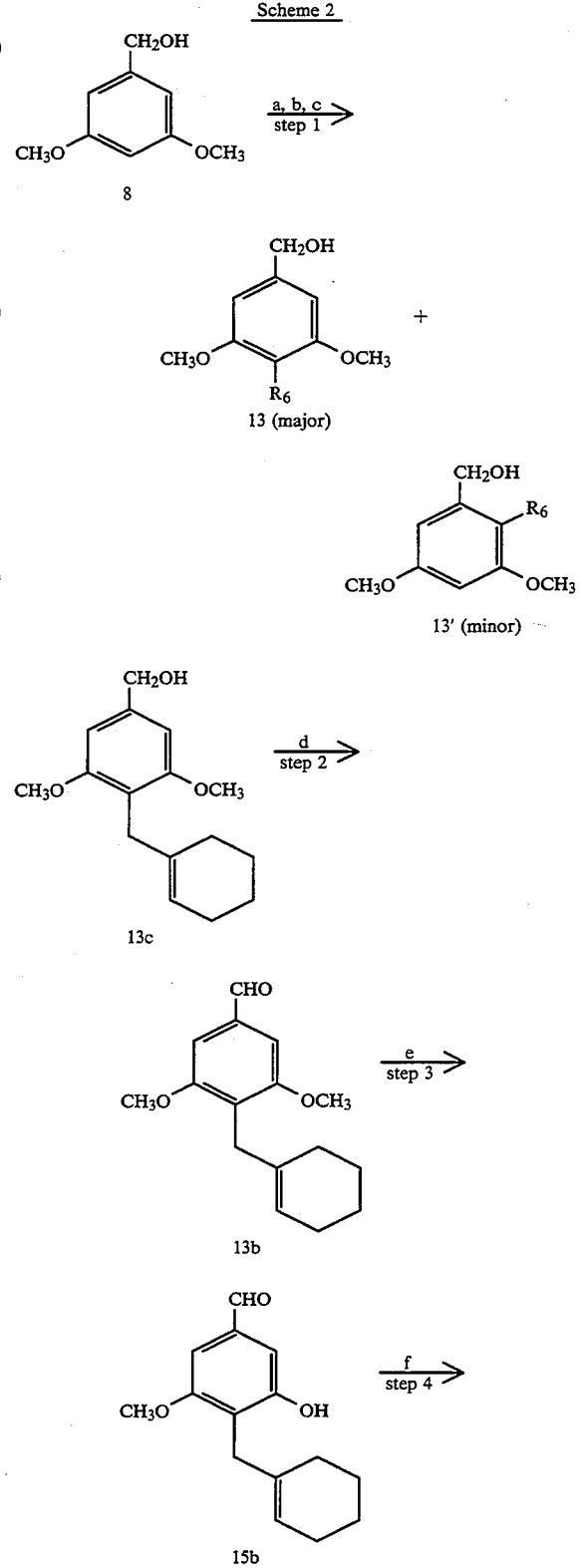

-continued
Scheme 2

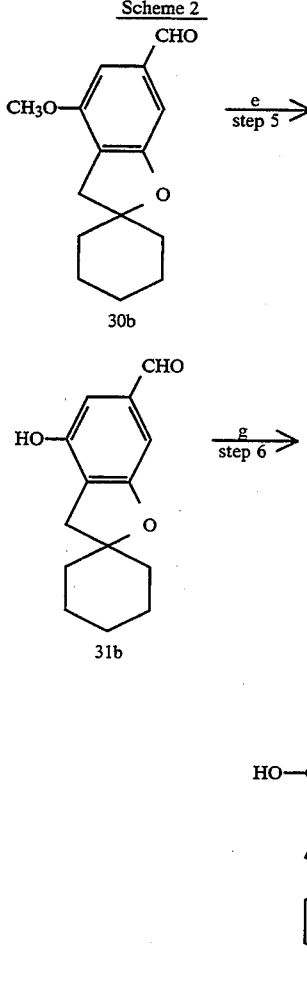

(a) $^n$BuLi, THF/TMEDA; (b) CuI; (c) R$_6$X;
(d) PCC, NaOAc, CH$_2$Cl$_2$; (e) $^t$BuSLi, HMPA;
(f) Amberlyst resin; (g) Ag$_2$O, aq. 5% NaOH reducing agents as lithium aluminum hydride, or diborane, preferably in an appropriate solvent such as an ether, e.g., THF, dioxane, or diethyl ether.

Even more complex dihydrobenzofuran-based compounds can be obtained by further modification of the analogs described above. Any of the compounds containing the methyl ether groups at the 4-position of the dihydrobenzofuran skeleton can be cleaved by one of the boron or thiolate reagents mentioned supra. Sometimes, as in the limonene series, it may be desirable to carry out the demethylation of the methyl ether with the carboxylic acid group at the 7-position protected as its alkyl ester (See, e.g., scheme 1) open positions in the phenyl ring may be metalated and functionalized as disclosed previously. The double bond of compound 20a can be hydroxylated by transition metal oxide reagents such as potassium permanganate or osmium tetroxide. The combination of methyl ether cleavage and hydroxylation of 20a, for example, would give compound 24a. Alternatively, compound 24a may be obtained by demethylation of intermediate 27c to the free phenol. In those instances, as in here, where an alkyl ester is employed to protect the carboxylic acid group at the 7-position, an alkaline, hydrolysis step may be necessary to obtain the free carboxylic acid (Scheme 1, step 1). Other modifications can

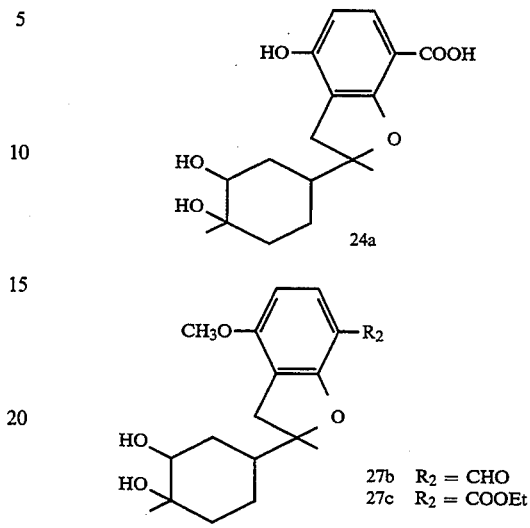

be envisioned which do not depart significantly from the scope and essence of the products of the present invention. Transformations such as epoxidation of the double bond, hydroxylation at the allylic position of the double bond, oxidative cleavage of the double bond, hydroformylations, and modifications of the products obtained therefrom are but a few non-limiting examples.

5.3. Demonstration of Complement Inhibition

The compounds of the invention can be assayed by any techniques known in the art in order to demonstrate their complement inhibiting activity. Such assays include but are not limited to the following in vitro tests for the ability to inhibit complement system activity or to selectively inhibit the generation of complement-derived peptides (See Section 6.25.1 for specific examples):

(i) measurement of inhibition of complement-mediated lysis of red blood cells (hemolysis); and
(ii) measurement of ability to inhibit formation of C5a and C5a des Arg and/or measurement of ability to inhibit formation of C3a and C3a des Arg.

Those compounds which are demonstrated to have significant complement-inhibiting activity can be therapeutically valuable for the treatment or prevention of diseases or disorders such as those described in Section 5.5, infra.

5.4. Demonstration of Immunosuppressive Activity

The compounds of the present invention can inhibit immune activity. In particular, the compounds of the invention inhibit cell-mediated immune function. For example, the compounds can suppress natural killer activity, inhibit the proliferation of peripheral blood lymphocytes, and/or inhibit the activation of T lymphocytes in PBL culture.

Any procedure known in the art may be employed to demonstrate immunosuppressive activity. Such procedures include but are not limited to in vitro assays for inhibition of natural killer lysis of target cells, inhibition of proliferation of peripheral blood lymphocytes, or inhibition of cell surface interleukin-2 receptor expression. Specific embodiments of assay procedures which can be used are detailed in the examples sections infra (See Subsections 6.261.1 through 6.26.4).

5.5. Therapeutic Uses of the Compounds of the Invention

The compounds of the invention which exhibit complement and/or immune activity inhibition have therapeutic value: in the prevention or treatment of various immune or inflammatory diseases or disorders. The compounds of the invention may be administered to a patient for treatment of an immune disorder or a disorder involving undesirable or inappropriate complement activity. In particular, an effective dose of an inhibitive compound of the invention may be therapeutically applied to ameliorate or prevent a detrimental effect caused by the activity of a component of the complement system (e.g., C5a) or an inappropriately reactive immune system. The diseases or disorders which may be treated by the compounds of the invention include but are not limited to those listed in Table III, supra. In particular, those disorders associated with extended zones of tissue destruction due to burn-or myocardial infarct-induced trauma, and adult respiratory distress syndrome (ARDS) also known as shock lung can be treated by administration of an effective amount of a compound of the invention.

Detrimental nonspecific activation of the complement system, or unfavorable activation by the alternative pathway, can also be prevented or treated by compounds of the invention. In specific embodiments, such compounds can ameliorate the acute pathological changes induced by specific or non-specific proteolytic processing of C5.

The compounds of the invention may also be used to modulate biologic or immune functions directly or indirectly mediated by the complement system, which can include but are not limited to those functions listed in Tables I and II, Supra, and the in vivo correlates of the in vitro functions therein.

In particular embodiments, the inhibitive compounds can be used to treat inflammations associated with, for example, kidney stones, systemic lupus erythematosis (SLE), nephrotoxic glomeronephritis, or multiple sclerosis (See, e.g., *Experimental Allergic Encephalomyelitis. A Useful Model for Multiple Sclerosis,* A Satellite Conference of the International Society of Neurochemists, Jul. 16-19, 1983, University of Washington, Seattle, Wash.; Miyazaki, W. et al. *Microbiol. Immunol.* 1980, 24, 1091; Konno, S. and Tsurutuji, S. *Br. J. Pharmacol.* 1983, 80, 269).

In yet another embodiment, the compounds of the invention can be administered for treatment of tissue damage due to myocardial ischemia and reperfusion, resulting from neutrophils attracted by and activated by the complement system.

The compounds of the invention may also be administered for the prevention or treatment of diseases or disorders caused or accompanied by increased lymphocyte or natural killer activity, including but not limited to atrophic gastritis, thyroiditis, allergic encephalomyelitis, gastric mucosa, thyrotoxicosis, autoimmune hemolytic anemia, pemphigus vulgaris, sympathetic ophthalmia, delayed-type hypersensitivity, rejection of allografts, graft-host reaction, organ transplant rejection, other autoimmune disorders, and drug allergies. They can also be used to alleviate the adverse effects of complement activation caused by therapeutic intervention such as tissue plasminogen activator therapy or cardiopulmonary bypass.

Pharmaceutical compositions comprising the inhibitive compounds or the salts thereof are provided by the present invention. Various delivery systems (e.g., encapsulation in liposomes, conjugation to specific antibodies) are known and can be used for therapeutic delivery of the compounds. Methods of administration include but are not limited to oral, intradermal, transdermal, intravenous, subcutaneous, intramuscular, intraperitoneal, and intranasal routes.

The invention can be better understood by referring to the following examples which are given for illustrative purposes only and are not meant to limit the invention.

6. Examples

6.1. 4-(1'-Cyclohexenyl)methyl-3,5-dimethoxybenzyl alcohol (13c)

Two equivalents of n-butyllithium (n-BuLi) were added slowly to a stirred solution of 3,5-dimethoxybenzyl alcohol (8, 10 equiv) and N,N,N'N'-tetramethylethylenediamine (TMEDA, 2.0 equiv) in anhydrous tetrahydrofuran (THF) at 0° C. After stirring at room temperature for 2 hours, the solution was cooled to $-78°$ C. and cuprous iodide (1.0 equiv) was added all at once. The suspension was allowed to warm up to $-45°$ C., stirred for 1.5 hours, and recooled to $-78°$ C. prior to the addition of 1-bromomethylcyclohexane (1.0 equiv) diluted with dry THF. The reaction mixture was then allowed to warm up gradually over a period of 6 hours and stirred at room temperature for up to 72 hours. The mixture was then quenched and washed several times with saturated aqueous sodium bicarbonate until the aqueous layer became colorless. The crude product mixture was recovered by evaporation of the solvent and was composed of the desired product 13c (80%), starting material 8 (15%), and the isomer 2-(1-cyclohexenylmethyl)-3,5-dimethoxybenzyl alcohol (13', 5%), as determined by proton NMR analysis. Thin layer chromatography (TLC) analysis (chloroform/ethyl acetate eluent, 30/20, v/v) likewise confirmed the presence of these three components with $R_f$ values of approximately 0.5, 0.4, and 0.6, respectively. Pure 13c was obtained by fractional crystallization from diethyl ether solutions. The fluffy white powder had a melting point of 61°–63° C. Analysis calculated for $C_{16}H_{22}O_3$: C 73.25; H, 8.45. Found: C, 73.21; H, 8.52. $^1H$ NMR (CDCl$_3$) δ6.54 (2H, s), 5.20 (1H, broad s), 4.59 (1H, s), 3.79 (6H, s), 3.26 (2H, broad s), 2.62 (1H, broad s), 1.93 (4H, m), and 1.56 (4H, m) in ppm downfield from tetramethylsilane (TMS). $^{13}C$ NMR (CDCl$_3$) δ 158.5 (2C's), 139.8, 136.3, 119.9 (2C's), 116.6, 102.5, 65.7, 55.8, 30.6, 28.8, 25.3, 23.1, and 22.5 in ppm downfield from TMS. IR(KBr) 3290 (br), 2930, 1590, 1460, 1425, 1210, 1140, and 1120 cm$^{-1}$.

6.2. 2-(1'-Cyclohexenyl)methyl-3-methoxymethoxyanisole (9a)

The 3-methoxymethoxyanisole, 7, was obtained in 96% yield by the following procedure. A mixture of finely powdered anhydrous potassium carbonate (2.0 equiv) and 3-methoxyphenol (1.0 equiv) in dry acetonitrile was stirred at 0° C. for 15 minutes under nitrogen. To ensure that the reaction pH remained above six, 100 ml of acetonitrile were used per gram of phenol substrate. A catalytic amount of 18-crown-6 (0.12 equiv) was added, and the mixture was stirred an additional 15 minutes at 0° C. Neat chloromethyl methyl ether (1.5 equiv) was then introduced slowly. The suspension was allowed to warm up to ambient temperature and stirred for 6 hours. After this time, the mixture was recooled to 0° C., and one-half the original quantities of $K_2CO_3$, 18-crown-6, and $CH_3OCH_2Cl$ were added. After another 4 hours of stirring at room temperature, the suspension was filtered, and the filtrate was concentrated under reduced pressure. The residue was dissolved in diethyl ether (Et$_2$O), washed with 5% sodium hydroxide (3×50 ml), concentrated in vacuo, and distilled under reduced pressure. Compound 7 was obtained as a clear colorless liquid. Bp 45° C. (0.15 mm Hg). $^1$H NMR (90 MHz, deuteriochloroform) δ 7.16 (1H, m), 6.61 (3H, m), 5.16 (2H, s), 3.79 (3H, s), and 3.49 (3H, s) in ppm downfield from TMS. $^{13}$C NMR(CDCl$_3$) δ 160.5, 158.2, 129.7, 108.2, 107.3, 102.5, 94.3, 55.9, and 55.1 in ppm downfield from TMS.

n-BuLi (1.1 equiv) was added slowly to a THF solution of compound 7 (1.0 equiv) and TMEDA (1.1 equiv), at 0° C. under a nitrogen atmosphere. The solution was stirred at room temperature for 2–5 hours and then cooled to −78° C. Cuprous iodide (1.2 equiv) was added all at once. The light gray suspension was warmed up to −40° C., and after stirring for 1.5 hours, turned into a green-gray color. The copper reagent was cooled to −78° C. and allowed to react with a THF solution of freshly-prepared allylic bromide 6a (1.3 equiv). The reaction mixture was allowed to warm up to ambient temperature gradually and stirred for up to 72 hours. The mixture was quenched and washed with a saturated aqueous solution of sodium bicarbonate as described previously in section 6.1. The organic layer was dried by passage through a plug of potassium carbonate and concentrated in vacuo to give a dark orange oil. The crude product was distilled under reduced pressure to provide compound 9a in 69% yield. Bp 105° C. (0.15 mm Hg). Anal. Calcd. for C$_{16}$H$_{22}$O$_3$: C, 73.25; H, 8.45. Found: C, 73.13; H, 8.50. $^1$H NMR (90 MHz, CDCl$_3$) δ 7.03 (1H, t, J=8 Hz), 6.71 (1H, d, J=8 Hz), 6.54 (1H, d, J=8 Hz), 5.23 (1H, broad s), 5.13 (2H, s), 3.77 (3H, s), 3.43 (3H, s), 3.32 (3H, broad s), 1.95 (4H, m), and 1.57 (4H, m) in ppm downfield from TMS. $^{13}$C NMR (75 MHz, CDCl$_3$) δ 158.5, 155.8, 136.3, 126.7, 120.0, 118.1, 107.0, 104.6, 94.3, 55.8 (2C's), 30.9, 28.8, 25.3, 23.1, and 22.6 ppm downfield from TMS. IR (neat) 2940, 2840, 1595, 1470, 1440, 1260, 1160, 1105, 1070, and 1025 cm$^{-1}$.

6.3. 3-(1'-Cyclohexenyl)methyl-2-hydroxy-4-methoxybenzoic acid (12a).

Compound 9a was metalated at the 4-position by the following procedure. A hexane solution of 9a (1.0 equiv) and TMEDA (1.1 equiv) was treated with a hexane solution of n-BuLi (1.1 equiv) added gradually at 0° C. under an atmosphere of nitrogen. The solution was stirred at room temperature for 3 hours and then cooled to −78° C.

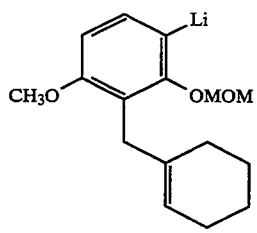

The aryllithium reagent Li-9a prepared by the above route was then exposed to a stream of dried carbon dioxide gas bubbled through the −78° C. solution for 0.5 hour. Carrying out this reaction at 0° C. cuts the resulting yield in half. The mixture was allowed to warm up to room temperature while maintaining a steady stream of gas. The mixture was poured into water and extracted a few times with 5% aqueous sodium hydroxide, then acidified to pH 1 with concentrated hydrochloric acid, and then extracted into ether. The crude product was back-extracted into Et$_2$O and the combined organic layers dried over magnesium sulfate. The solvent was evaporated and the residue redissolved in a minimum of boiling ether. The warm solution was allowed to cool slightly, and then hexane was added to the point of cloudiness. The mixture was then allowed to stand in the freezer. An off-white solid with a melting point of 161°–163° C. was harvested (66% yield). Anal. Calcd. for C$_{15}$H$_{18}$O$_4$: C, 68.69; H, 6.92. Found: C, 68.75; H, 6.95. $^1$H NMR (90 MHz, acetone-d$_6$) δ 7.81 (1H, d, J=9 Hz), 6.62 (1H, d, J=9 Hz), 5.26 (1H, broad s), 4.26 (2H, broad s), 3.90 (3H, s), 3.29 (2H, broad s), 2.01 (4H, m), and 1.57 (4H, m) in ppm downfield from TMS. $^{13}$C NMR (acetone-d$_6$) δ 173.0, 164.3, 162.1 (2C's), 136.5, 130.6, 121.0, 115.9, 106.5 (2C's), 103.3, 56.3, 30.0, 29.4, 25.8, 23.8, 23.2 (2C's). IR (KBr) 1650, 1610, 1500, 1455, 1265, 1185, and 1090 cm$^{-1}$.

6.4. 3-(1'-Cyclohexenyl)methyl-2-hydroxy-4-methoxybenzaldehyde (12b)

A solution of aryllithium reagent Li-9a, prepared in situ by the procedure described in Section 6.3, vide supra, was cooled to −12° C. and treated with neat N,N'-dimethylformamide (1.5 equiv) added all at once. The mixture was stirred at room temperature for 3 hours. The mixture was then poured into water, saturated with sodium chloride, and extracted with Et$_2$O. The organic layers were combined, dried (MgSO$_4$), and concentrated in vacuo; the residue was recrystallized from ether/hexane (See Section 6.3). The product was purified by column chromatography (silica, ether/hexane eluent). Mp 48°–49° C. Anal. Calcd. for C$_{15}$H$_{18}$O$_3$: C, 73.15; H, 7.37. Found: C, 73.22; H, 7.40. $^1$H NMR (CDCl$_3$) δ 11.42 (1H, broad s), 9.64 (1H, s), 7.33 (1H, d), 6.51 (1H, d), 5.23 (1H, broad s), 3.83 (3H, s), 3.26 (2H, broad s), 1.96 (4H, m), and 1.56 (4H, m) in ppm downfield from TMS. $^{13}$C NMR (CDCl$_3$) δ 194.7, 164.6, 161.3, 135.5, 133.8, 120.6, 115.9, 115.6, 103.1, 55.9, 29.9, 28.8, 25.2, 23.0, and 22.4 in ppm downfield from TMS. IR (KBr) 2930, 2840, 1625, 1495, 1255, 1100, 800, and 640 cm$^{-1}$.

6.5. 3-(1'-Cyclohexenyl)methyl-2-methoxymethoxy-4-methoxy-N-methylbenzamide (10b) and -N-tert-butylbenzamide (10c)

A solution of Li-9a, prepared by the procedure of Section 6.3, was cooled to −78° C. and treated with methylisocyanate (1.2 equiv). The mixture was allowed to warm up gradually to ambient temperature and stirred for 8 hours. The mixture was then poured into water, saturated with sodium chloride, and extracted with Et$_2$O. The organic layers were combined, dried (MgSO$_4$), and concentrated in vacuo; the residue was recrystallized from ether/hexane (See Section 6.3). Compound 10b was obtained in 61% yield as a white solid. Mp 99°–100° C. Anal. Calcd. for C$_{18}$H$_{25}$NO$_4$: C, 67.69; H, 7.89; N 4.39. Found: C, 67.59; H, 7.93; N, 4.33. $^1$H NMR (CDCl$_3$) δ 7.97 (1H, d, J=9 Hz), 7.56 (1H, broad s), 6.79 (1H, d, J=9 Hz), 5.09 (1H, broad s), 4.96 (2H, s), 3.80 (3H, s), 3.51 (3H, s), 3.30 (2H, broad s), 2.99 (3H, d, J=5 Hz), 1.96 (4H, broad m), and 1.60 (4H, broad m) in ppm downfield from TMS. $^{13}$C NMR (CDCl$_3$) δ 166.6, 161.1, 153.9, 136.0, 130.3, 122.1, 120.5, 120.0, 107.1, 100.8, 58.3, 55.9, 26.5, 31.7, 29.2, 25.2, 23.0, and 22.5 in ppm downfield from TMS. IR (KBr) 3340, 2930, 1635, 1595, 1530, 1470, 1275, 1160, 1100, 1065, 980, 945, and 825 cm$^{-1}$. The free phenol 3-(1'-cyclohexenyl)methyl-2-hydroxy-4-methoxy-$\underline{N}$-methylbenzamide, 12c, was obtained by removal of the methoxymethyl protecting group of 10b by stirring in 5% HCl/ether overnight (See, Section 6.9): Mp 138°–139° C. Anal. Calcd. for $C_{16}H_{21}NO_3$: C, 69.79; H, 7.69; N, 5.09. Found: C, 69.71; H, 7.75; N, 5.04. $^1$H NMR (CDCl$_3$) δ 12.57 (1H, s), 7.26 ($^1$H, d, J=9 Hz), 6.41 (1H, d, J=9 Hz), 6.24 (1H, broad s), 5.23 (1H, broad s), 3.84 (3$\underline{H}$, s), 3.31 (2H, broad s), 2.98 (3H, d, J=5 Hz), 1.96 (4H, broad m), and 1.58 (4H, broad m) in ppm downfield from TMS. $^{13}$C NMR (CDCl$_3$) δ 170.9, 161.9, 160.8, 135.9, 124.2, 120.1, 116.5, 107.9, 101.6, 55.7, 26.4, 30.3, 28.9, 25.2, 23.1, and 22.5 in ppm downfield from TMS. IR (KBr) 3400, 2940, 1650, 1590, 1550, 1495, 1430, 1375, 1315, 1275, 1195, 1100, and 1050 cm$^{-1}$.

In contrast, when the methylisocyanate electrophile was added to the solution of Li-9a at 0° C., instead of at −78° C., a different product, the 1,3-benzoxazine-2,4-dione derivative 10e was isolated in 40% yield. The structure of this compound was confirmed by spectroscopy and elemental analyses Mp 132°–133° C. Anal. Calcd. for $C_{17}H_{19}NO_4$: C, 67.76; H, 6.36; N, 4.65. Found: C, 67.67; H, 6.41; N, 4.62. $^1$H NMR (CDCl$_3$) δ 7.96 (1H, d), 6.89 (1H, d), 5.23 (1H, broad s), 3.92 (3H, s), 3.43 (3H, s), 3.38 (2H, broad s), 1.92 (4H, broad m), and 1.57 (4H, broad m) in ppm downfield from TMS. $^{13}$C NMR (CDCl$_3$) δ 163.5, 160.9, 151.6, 148.7, 134.7, 127.1, 121.6, 116.1, 108.1, 107.2, 56.2, 30.3, 28.7 (2C's), 25.2, 22.9, and 22.3 in ppm downfield from TMS. IR (KBr) 2930, 1745, 1695, 1620, 1595, 1425, 1375, 1275, 1205, 1095, and 755 cm$^{-1}$. MS (m/e) 301, 221, 163, and 81. When tert-butylisocyanate is substituted for methylisocyanate in the procedure described above, the N-tert-butylbenzamide derivative 10c is obtained in good yield. $^1$H NMR (CDCl$_3$) δ 7.91 (1H, d, J=9 Hz), 7.61 (1H, broad s), 6.73 (1H, d, J=9 Hz), 5.09 (1H, broad s), 4.94 (2H, s), 3.80 (3H, s), 3.56 (3H, s), 3.31 (2H, broad s), 1.96 (4H, m), 1.58 (4H, m), and 1.48 (9H, s) in ppm downfield from TMS.

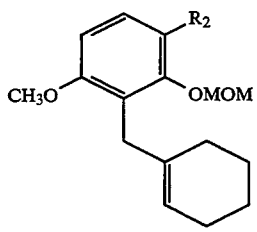

| | |
|---|---|
| $R_2 = -COOH$ | 10a |
| $R_2 = -CONHCH_3$ | 10b |
| $R_2 = -CONH^tBu$ | 10c |
| $R_2 = -CH_2OH$ | 10d |

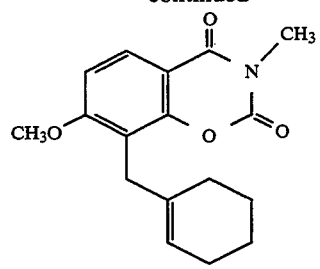

Deprotection of 10c yielded the free phenol, 3-(1'-cyclohexenyl) methyl-2-hydroxy-4-methoxy-$\underline{N}$-tert-butylbenzamide, 12d, with the following proton NMR data: $^1$H NMR (CDCl$_3$) δ7.19 (1H, d, J=9 Hz), 6.32 (1H, d, J=9 Hz), 6.03 (1H, broad s), 5.23 (1H, broad s), 3.79 (3$\underline{H}$, s), 3.28 (2H, broad s), 1.96 (4H, m), 1.56 (4H, m), and 1.46 (9H, s) in ppm downfield from TMS.

6.6. 3-(1'-Cyclohexenyl)methyl-4-methoxy-2-methoxymethoxybenzyl alcohol (10d) 9

By a procedure similar to those outlined in Sections 6.3–6.5, compound 10d was obtained by allowing the aryllithium reagent Li-9a to react with paraformaldehyde at low temperature. Chromatographic purification gave 10d (64%) as a light yellow oil. Anal. Calcd. for $C_{17}H_{24}O_4$: C, 69.84; H, 8.27. Found: C, 69.70; H, 8.24. $^1$H NMR (CDCl$_3$) δ 7.22 (1H, d, J=9 Hz), 6.68 (1H, d, J=9 Hz), 5.13 (1H, m), 4.93 (2H, s), 3.79 (3H, s), 3.57 (3H, s), 3.26 (2H, broad s), 1.94 (4H, m), and 1.58 (4H, m) in ppm downfield from TMS. $^{13}$C NMR (CDCl$_3$) δ 158.9, 156.0, 136.3, 128.6, 127.3, 122.1, 120.8, 107.2, 99.9, 61.1, 57.2, 55.8, 32.0, 29.1, 25.2, 23.0, and 22.6 in ppm downfield from TMS. IR (neat) 3410 (broad), 2930, 1600, 1490, 1270, 1160, 1065, 990, and 815 cm$^{-1}$.

6.7. 7-Carboxyl-4-methoxyspiro[benzofuran-2(3H)-cyclohexane] (11a)

A benzene solution of compound 12a (Section 6.3) was treated with dry Amberlyst ion-exchange resin (approximately 3–4 g per gram of substrate, dried at 110° C. under high vacuum) added in one portion. The mixture was stirred for up to 24 hours at room temperature and then filtered. The resin beads were washed thoroughly with fresh benzene and methylene chloride. The filtrates were combined, washed with water, dried over magnesium sulfate, and concentrated in vacuo. The product 11a was purified in 85% yield by column chromatography. Mp 192°–194° C. Anal. Calcd. for $C_{15}H_{18}O_4$: C, 68.69; H, 6.92. Found: C, 68.52; H, 6.99. $^1$H NMR (CDCl$_3$) δ broad roll centered at about 12.0 (1H), 7.85 (1H, d, J=9 Hz), 6.50 (1H, d, J=9 Hz), 3.89 (3H, s), 2.94 (2H, s), and 1.69 (10H, broad m) in ppm downfield from TMS. $^{13}$C NMR (CDCl$_3$) δ 164.5, 160.6, 158.7, 132.7, 113.6, 106.2, 104.5, 94.2, 55.7, 38.0, 37.1 (2C's), 24.9, and 23.2 (2C's) in ppm downfield from TMS. FIG. 1 shows the infrared (KBr) spectrum. IR (KBr) 1660, 1615, 1445, 1435, 1385, and 1100 cm$^{-1}$. Cyclization was also accomplished by heating the phenol precursor in either a 50/50 4N hydrochloric acid/isopropanol solvent mixture or a boron trifluoride etherate solution in THF. This latter cyclization procedure is not recommended for any phenol precursor other than 12a, however.

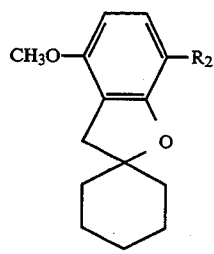

| | |
|---|---|
| $R_2 = -COOH$ | 11a |
| $R_2 = -CHO$ | 11b |
| $R_2 = -CONHCH_3$ | 11c |
| $R_2 = -CONH^tBu$ | 11d |
| $R_2 = -CH_2OH$ | 11e |

6.8. 7-Formyl-4-methoxyspiro[benzofuran-2(3H)-cyclohexane] (11b)

The phenol precursor 12b was treated with Amberlyst resin as described in the previous section. The product 11b was isolated and purified by column chromatography (83% yield). Mp 62°–63° C. Anal. Calcd. for $C_{15}H_{18}O_3$: C, 73.15; 7.37. Found: C, 73.22; H, 7.40. $^1$H NMR (CDCL$_3$) δ 10.16 (1H, s), 7.66 (1H, d, J=9 Hz), 6.46 (1H, d, J=9 Hz), 3.88 (3H, s), 2.88 (2H, s), 1.4–2.0 (10H, broad m).

Compound 11b is easily transformed to 11e by a metal hydride reduction step or other means well-known in the art.

6.9. 4-Methoxyspiro[benzofuran-2-(3H)-cyclohexane]-7-N-methylcarboxamide (11c)

Compound 10b was deprotected by stirring it overnight in a 50/50 4N hydrochloric acid/isopropanol solvent mixture at room temperature. The volatile components of the mixture were then removed under vacuum, and the residue was taken up in ether. The solution was dried over magnesium sulfate and filtered. The solvent was removed and the residue was dissolved in benzene and treated with Amberlyst resin as described previously in Section 6.7. After 7 days of stirring at room temperature, the cyclized product 11c was obtained in 94% yield. Mp 147°–148° C. (ether). Anal. Calcd. for $C_{16}H_{21}NO_3$: C, 69.79; H, 7.69; N, 5.09. Found: C, 69.7; H, 7.75; N, 5.05. $^1$H NMR (CDCl$_3$) δ 7.97 (1H, d, J=9 Hz), 7.52 (1H, broad s), 6.49 (1H, d, J=9 Hz), 3.84 (3H, s), 2.99 (3H, d, J =5 Hz), 2.90 (2H, s), and 1.46–1.90 (10H, broad m) in ppm downfield from TMS. $^{13}$C NMR (CDCl$_3$) δ 165.5, 158.9, 157.5, 131.1, 113.4, 109.8, 103.4, 92.0, 55.5, 37.9, 37.2 (2C's), 26.3, 25.0, and 23.3 (2C's) in ppm downfield from TMS. IR (KBr) 3370, 2940, 1620, 1530, 1495, 1285, 1220, 1100, and 775 cm$^{-1}$. The tert-butylcarboxamide derivative 11d is obtained from 10c utilizing the same method.

6.10. 7-Carboxyl-4-hydroxyspiro[benzofuran 2-(3H)-cyclohexane] (14a)

Cyclized product 11a obtained from Section 6.7 was converted to the free phenol by the following procedure. A solution of 2-methyl-2-propanethiol (5.2 equiv) in hexamethylphosphoric acid triamide (HMPA) was treated with n-BuLi (5.0 equiv) at room temperature under an atmosphere of N$_2$. After stirring for 20 minutes this reagent solution was added to an HMPA solution of the methoxy derivative 11a (1.0 equiv) under an inert atmosphere. The mixture was stirred up to 96 hours at room temperature. The reaction mixture was then poured into 5% aqueous sodium hydroxide, stirred for 15 minutes and washed twice with Et$_2$O. The basic aqueous layer was acidified with concentrated hydrochloric acid at 0° C., followed by back-extraction into three portions of Et$_2$O. The organic extracts were combined, washed twice with 5% aqueous hydrochloric acid, dried over magnesium sulfate, and concentrated in vacuo. The product 14a was obtained after column chromatography (31%). Mp 173°–174° C. High-resolution mass spectrometry: Exact Mass Calcd., 248. 10486 amu. Observed, 248.10486±0.00073 amu. $^1$H NMR (acetone-d$_6$) δ 7.62 (aH, d, J=9 Hz), 6.47 (1H, d, J=]Hz), 3.92 (2H, broad s), 2.93 (2H, s), and 1.66 (10H, broad m) in ppm downfield from TMS. $^{13}$C NMR (acetone-d$_6$) δ 166.3, 162.1, 159.6, 132.6, 113.7, 109.1, 105.9, 92.1, 38.2, 37.7, 25.7, and 23.7 in ppm downfield from TMS. IR (KBr) 3240, 2930, 1705, 1610, 1450, 1385, 1265, 1215, 1050, 895, 830, and 785 cm$^{-1}$.

6.11. 7-Formyl-4-hydroxyspiro[benzofuran-2(3H)-cyclohexane] (14b)

The formyl derivative 14b was obtained from cyclized product 11b by the method outlined in Section 6.10. Mp 142°–143° C. Anal. Calcd. for $C_{14}H_{16}O_3$: C, 72.39; H, 6.94. Found: C, 72.42; H, 6.97. $^1$NMR (CDCl$_3$) δ 10.1 (1H, s), 7.53 (1H, d, J=9 Hz), 6.43 (1H, d, J=9 Hz), 2.92 (2H, s), and 1.71 (10H, broad m) in ppm downfield from TMS. $^{13}$C NMR (CDCl$_3$) δ 186.7, 164.8, 161.1, 128.6, 114.3, 113.6, 109.9, 92.4, 38.0, 37.7 (2C's), 25.7, and 23.6 (2C's) in ppm downfield from TMS. IR (KBr) 3200, 2930, 2860, 1660, 1615, 1590, 1500, 1450, 1380, 1305, 1265, 1225, 1145, and 1040 cm$^{-1}$.

Compound 14a was also prepared from silver oxide oxidation (See Section 6.13, infra.) of 14b in 4N sodium hydroxide (80° C., 3 days). The 7-hydroxymethyl-4-hydroxyspiro[benzofuran-2(3H)-cyclohexane](14c) may also be prepared from 14b using LAH in ether.

6.12. 4-(1'-Cyclohexenyl)methyl-3,5-dimethoxy-benzaldehyde (13b)

A mixture of 13c (0.300 g, 1.14 mmol), pyridinium chlorochromate (PCC 0.500 g, 2.32 mmol), and sodium acetate (0.040 g, 0.48 mmol) in methylene chloride (60 ml) was stirred at room temperature for 16 hours. Afterwards, the mixture was diluted with an equal volume of ether, filtered, and concentrated in vacuo. The residue was redissolved in ether, refiltered, and washed with aqueous saturated sodium bicarbonate (3×15 ml). The organic layer was filtered through a short Florisil column and concentrated in vacuo. The residual solid was recrystallized from hexane to give white needles of 13b (0.278 g, 93%). Mp 75°–76° C. Anal. Calcd. for $C_{16}H_{20}O_3$: C, 73.82; H, 7.74. Found: C, 73.79; H, 7.76. $^1$H NMR (CDCl$_3$) δ 9.89 (1H, s), 7.07 (2H, s), 5.20 (1H, broad s), 3.88 (6H, s), 3.31 (2H, broad s), 1.92 (4H, m), and 1.56 (4H, m) in ppm downfield from TMS. $^{13}$C NMR (CDCl$_3$) δ 191.9, 158.9 (2C's), 135.6, 135.5, 125.0, 120.8, 105.0 (2C's), 56.0, 31.1, 28.9, 25.3, 23.1, and 22.4 in ppm downfield from TMS. IR (KBr) 2930, 1690, 1590, 1460, 1420, 1380, 1310, 1210, 1140, 1115, 835 cm$^{-1}$.

6.13. 4-(1'-Cyclohexenyl)methyl-3-hydroxy-5-methoxybenzaldehyde (15b) and 4-(1'-cyclohexenyl)-methyl-3-hydroxy-5-methoxybenzoic acid (15a)

Compound 13b (0.102 g, 0.39 mmol) was demethylated by the procedure outlined in Section 6.10, using t-BuSLi (2.9 mmol) in HMPA (6 ml). The chloroform solution of the crude oil was passed through a silica gel column and concentrated in vacuo. The residual solid was recrystallized from ether/hexane to give 15b as fine needles (0.099 g, 93%). Mp 155°–156° C. Anal. Calcd. for $C_{15}H_{18}O_3$: C, 73.15; H, 7.37. Found: C, 73.21; H, 7.40. $^1$H NMR (CDCl$_3$) δ 9.88 (1H, s), 7.01 (2H, s), 5.83 (1H, broad s), 5.62 (1H, broad s), 3.87 (3H, s), 3.44 (2H, broad s), 1.97 (4H, m), and 1.60 (4H, m) in ppm downfield from TMS. $^{13}$C NMR (CDCl$_3$) δ 191.9, 158.8, 156.6, 136.1, 136.0, 123.7, 120.8, 112.3, 102.1, 56.0, 32.2, 28.0, 25.2, 22.6, and 22.1 in ppm downfield from TMS. IR (KBr) 3240, 2930, 1670, 1595, 1515, 1400, 1320, 1210, 1145, 1100, 840, and 710 cm$^{-1}$.

A mixture of compound 15b (0.246 g, 1.0 mmol) and silver (I) oxide (0.350 g, 1.5 mmol) in 8 ml of aqueous 5% sodium hydroxide was stirred for 16 hours at room temperature. Afterwards the mixture was filtered, and the residue was washed thoroughly with aqueous 5% sodium hydroxide. The filtrates were combined, cooled, and acidified with cold concentrated hydrochloric acid. The resulting aqueous solution was extracted with ether (3×25 ml). The combined ether layers were dried (MgSO$_4$) and concentrated in vacuo. The residual solid was recrystallized from ether/acetone to give 0.245 g of 15a (94%). Mp 152°–153° C. Anal. Calcd. for $C_{15}H_{18}O_4$: C, 68.69; H, 6.92. Found: C, 68.80; H, 6.97. $^1$H NMR (acetone-d$_6$) δ 7.26 (1H, d, J=2 Hz), 7.14 (1H, d, J=2 Hz), 5.26 (1H, broad s), 3.82 (3H, s), 3.72 (2H, broad s), 3.31 (2H, broad s), 1.96 (4H, broad m), and 1.57 (4H, broad m) in ppm downfield from TMS. $^{13}$C NMR (CDCl$_3$) δ 168.0, 159.6, 156.9, 136.5, 130.2, 121.0, 120.9, 110.4, 104.0, 56.1, 31.6, 29.4, 25.8, 28.8, and 23.2 in ppm downfield from TMS. IR (KBr) 3390, 2930, 1690, 1585, 1425, 1315, 1100, and 775 cm$^{-1}$.

6.14. 6-Carboxyl-4-methoxyspiro[benzofuran-2-(3H)-cyclohexane](30a) and 6-formyl-4-methoxyspiro [benzofuran-2-(3H)-cyclohexane] (30b)

Using the cyclization procedure outlined in Section 6.7, compound 15a (0.070 g) was converted with the aid of Amberlyst resin to the cyclized compound 30a. The crude product was purified by chromatography and recrystallized from ether/acetone to give 0.064 g (91%) of 30a as off-white crystals. Mp 202°–203° C. High-resolution mass spectrometry: Exact Mass Calcd., 262.12051 amu. Observed, 262.12052±0.00089 amu. $^1$H NMR (acetone-d$_6$) δ 7.13 (1H, s), 7.00 (1H, s), 3.87 (3H, s), 3.58 (1H, broad s), 2.91 (2H, s), and 1.63 (10H, broad m) in ppm downfield from TMS. $^{13}$C NMR (acetone-d$_6$) δ 167.7, 160.9, 157.3, 132.8, 119.8, 105.8, 104,8, 90.5, 55.9, 39.1, 37.8 (2C's), 25.7, and 23.6 (2C's) in ppm downfield from TMS. IR (KBr) 2930, 1675, 1600, 1425, 1330, 1275, 1220, 1125, 1035, 950, 780 and 735 cm$^{-1}$.

Similarly compound 15b (0.050 g) was cyclized and purified by chromatography and recrystallization (ether/hexane) to give compound 30b in 96% yield (0.048 g). Mp 88°–89° C. Anal. Calcd. for $C_{15}H_{18}O_3$: C, 73.15; H, 7.37. Found: C, 73.21; H,. 7.40. $^1$H NMR (CDCl$_3$) δ 9.87 (1H, s), 6.94 (1H, s), 6.90 (1H, s), 3.88 (3H, s), 2.82 (2H, s) and 1.70 (10H, broad m) in ppm downfield from TMS. $^{13}$C NMR (CDCl$_3$) δ 191.8, 160.5, 1.56.9, 138.2, 121.3, 105.6, 102.8, 90.4, 55.6, 38.5, 37.2 (2C's), 25.1, and 23.0 (2C's). IR (KBr) 2940, 2850, 1690, 1600, 1325, 1220, 1130, 1110, 1035, 835, and 685 cm$^{-1}$.

6.15. 6-Formyl-4-hydroxyspiro[benzofuran-2-(3H)-cyclohexane] (31b) and 6-carboxyl-4-hydroxyspiro[benzofuran-2-(3H)-cyclohexane] (31a)

Following the procedure outlined in Section 6.10, compound 30b (0.201 g, 0.82 mmol) was demethylated using t-BuSLi (2.4 mmol) in HMPA (7 ml). The crude oil was dissolved in chloroform and passed through a column of silica gel. The filtrate was concentrated in vacuo, and the residue was recrystallized from ether/hexane to give 0.165 g (87%) of 31b as fine needles. Mp 115°–116° C. High-resolution mass spectrometry: Exact Mass Calcd., 232.10994 amu. Observed, 232.10996±0.00081 amu. $^1$H NMR (CDCl$_3$) δ 9.00 (1H, s), 6.90 (1H, s), 6.85 (1H, s), 2.97 (2H, s), and 1.9–1.3 (10H, broad m) in ppm downfield from TMS. $^{13}$C (CDCl$_3$) δ 192.2, 161.2, 153.2, 138.0, 120.3, 108.6, 104.3, 90.4, 38.1, 37.2 (2C's), 25.0 and 23.0 (2C's) in ppm downfield from TMS. IR (KBr) 3250, 2930, 1665, 1585, 1305, 1280, 1250, 1205, 1175, 840, 805, and 740 cm$^{-1}$.

Compound 31b (0.048 g, 0.21 mmol) was then oxidized in a suspension of silver(I) oxide (0.120 g, 0.52 mmol) in aqueous 5% sodium hydroxide (5 ml) as in Section 6.13. The product was recrystallized from acetone/ether to give 0.049 g (96%) of 31a as an off-white powder. Mp 221°–222° C. High-resolution mass spectrometry: Exact Mass Calcd., 248.10486 amu. Observed, 248.10498±0.00085 amu. $^1$H NMR (acetone-d$_6$) δ 7.08 (1H, s), 6.87 (1H, s), 3.73 (1H, broad s), 2.94 (2H, s), and 1.75 (10H, broad m) in ppm downfield from TMS. $^{13}$C NMR (acetone-d$_6$) δ 167.9, 161.3, 154.9, 132.4, 118.6, 109.9, 103.0, 90.1, 39.0, 37.8 (2C's), 25.7, and 23.6 (2C's) in ppm downfield from TMS. IR (KBr) 3300, 2940, 1720, 1610, 1435, 1225, 1200, 1060, and 965 cm$^{-1}$.

6.16. (+)-1-Methoxy-3-methoxymethoxy-2-[2-(4'-methylcyclohex-3'-en-1'R-yl) prop-2-enyl]benzene ((+)-9b) and ((−)-9b)

A solution of triphenylphosphine (8.474 g, 0.032 mol) and either R-(+)-or S-(−)-limonenyl alcohol (4.420 g, 0.029 mol), prepared by the method of Crawford and co-workers (See, Section 5.2.1, supra), in 20 ml of a 1:1 methylene chloride/carbon tetrachloride solvent mixture was heated under reflux for 3 hours under an inert atmosphere. The resulting mixture was allowed to cool, and the solvents were removed carefully under reduced pressure. Hexane (70 ml) was added to the residue and the suspension was filtered. The solid triphenylphosphine oxide was washed with fresh hexane (2×70 ml), and the filtrates were combined and concentrated in vacuo. The residual oil was purified by fractional distillation under reduced pressure to provide the desired homochiral limonenyl chloride, 6b, in 91% yield. Bp 108° C. (0.25 mm Hg). $[\alpha]^{25}_D$ (CHCl$_3$)=+84.8° (c=0.21) for the R-(+)-6b and −84.1° (c=0.44) for the S-(−)-6b. $^1$H NMR (CDCl$_3$) δ 5.42 (1H, broad s), 5.16 (1H, broad s), 5.00 (1H, broad s ), 4.10 (2H, s ), and 1.66 (3H, s) in ppm downfield from TMS. $^{13}$C NMR (CDCl$_3$) δ 149.62, 133.81, 120.21, 113.09, 47.79, 36.53, 31.20, 30.42, 28.03, and 23.42 in ppm downfield from TMS.

A THF/TMEDA solution of the aryl copper reagent derived from 3-methoxymethoxyanisole, 7 (11.9 mmol), was prepared according to Section 6.2 and cooled to −78° C. A THF solution of homochiral 6b (14.9 mmol) was then added under an inert atmosphere. The mixture was allowed to warm up to room temperature very gradually and stirred for 1 day. The reaction mixture was quenched with a saturated aqueous solution of sodium bicarbonate and stirred for 3 hours. The phases were separated, and the aqueous layer was extracted several times with ether. The organic fractions were combined, dried (MgSO$_4$), and concentrated in vacuo. The residue was filtered through a short column of silica to remove any remaining copper salts and subsequently distilled. A portion of the excess 6b was recovered first followed by the desired (+)-9b or (−)-9b (93% yield). Bp 132° C. (0.3 mm Hg). $[\alpha]^{25}_D$ (CHCl$_3$)= +57.5° (c=0.16) and −56.6° (c=0.64) for the dextrorotatory and levorotatory enantiomers, respectively. Anal. Calcd. for C$_{19}$H$_{26}$O$_3$: C, 75.50; H, 8.70. Found: C, 75.39; H, 8.69 ((+)-9b) and C, 8.69; H, 75.45 ((−)-9b). $^1$H NMR (CDCl$_3$) δ 7.13 (1H, t, J=8.1 Hz), 6.73 (1H, d, J=8.1 Hz), 6.58 (1H, d, J=8.1 Hz), 5.43 (1H, broad s), 5.14 (2H, s), 4.67 (1H, broad s), 4.34 (1H, broad s), 3.78 (3H, s), 3.43 (3H, s), 3.40 (2H, s), and 1.66 (3H, s) in ppm downfield from TMS. $^{13}$C NMR (CDCl$_3$) δ 158.65, 156.02, 153.03, 133.71, 127.11, 120.97, 118.03, 107.07, 106.43, 10.4.72, 94.44, 56.01, 55.87, 40.46, 31.30, 30.81, 28.27, 28.19, and 23.51 in ppm downfield from TMS.

6.17. 4-R-(+)-(3-Chloropropen-2-yl)-1-methyl -1S,2R-cyclohexanediol acetonide ((+)-6c)

The carveol epoxide 2S,3S-epoxy-5-R-isopropenyl-2-methyl-R-cyclohexanol was prepared from (−)-carvone by the method of Itoh, A. et al. (*Bull. Soc. Chim. Jap.* 1980, 53, 2357). An anhydrous THF (10 ml) solution of the epoxide (2.500 g, 0.015 mol) was added dropwise, at room temperature, to a stirred THF (40 ml) suspension of LAH (0.566 g, 0.015 mol) under a nitrogen atmosphere. The mixture was stirred for 4–6 hours and then cooled to 0° C. Small pieces of ice were carefully added until no more hydrogen was evolved. Cold aqueous 6N hydrochloric acid was then added to dissolve any colloidal metal salts. The resulting product mixture was extracted with ether (4×50 ml), dried, and concentrated in vacuo. The residual solid was purified by sublimation (67°–71° C./1.5 mm Hg) to provide white crystals of 4-R-(+)-isopropenyl-1-methyl-1S,2R-cyclohexanediol. Additional carveodiol product was obtained by sequential column chromatography and sublimation of the residual oil from the first sublimation procedure. The combined yield was 2.230 g (88% yield). Mp 71.5°–72.0° C. $[\alpha]^{25}_D$ (CHCl$_3$)= +6.67° (c=0.45). $^1$H NMR (CDCl$_3$) δ 4.68 (2H, s), 3.50 (1H, m), 1.69 (3H, s), and 1.26 (3H, s) in ppm downfield from TMS. IR (KBr) 3290, 2990, 2820, 1635, 1440, 1370, 1150, 1060, 1010, and 880 cm$^{-1}$.

The corresponding acetonide was prepared by stirring a solution of the carveodiol (1.900 g, 0.011 mol), 2,2-dimethoxypropane (8.05 g, 0.077 mol), and p-toluenesulfonic acid monohydrate (68 mg, 0.36 mmol) in 30 ml of dry acetone overnight at room temperature and under a dry atmosphere. A 2N aqueous sodium hydroxide solution (10 ml) was added to the reaction mixture followed by ether (100 ml). The phases were separated, and the aqueous layer was extracted with fresh ether (3×100 ml). The extracts were combined, dried, and concentrated in the usual manner. Purification by column chromatography provided 1.925 g (82%) of 4-R-(+) -isopropenyl-1-methyl-1S,2R-cyclohexanediol acetonide as an oil $[\alpha]^{25}_D$ (CHCl$_3$)= +1.426° (c=0.65) $^1$H NMR (CDCl$_3$) δ 4.78 (1H, s), 4.72 (1H, s), 3.95 (1H, t, J=3 Hz), 1.76 (3H, s), 1.48 (3H, s), 1.40 (3H, s), and 1.36 (3H, s) in ppm downfield from TMS. $^{13}$C NMR (CHCl$_3$) δ 149.20, 190.20, 107.59, 79.65, 79.19, 39.07, 34.22, 31.92, 28.94, 27.75, 27.42, 24.92, and 20.71 ppm downfield from TMS. IR (neat) 3010–2820, 1638, 1450, 1370, 1205, 1180, 1050, and 890 cm$^{-1}$.

Finally, a stirred methylene chloride (280 ml) solution of the above acetonide (2.050 g, 0.01 mol) was treated with a 1.03M aqueous solution of calcium hypochlorite (10 ml) at 0° C. Small pieces of dry ice were added to the reaction mixture over a 2 hour period. The organic phase was then separated, dried, and concentrated in vacuo. The product mixture was purified by a combination of column chromatography and fractional distillation to give (+)-6c (1.630 g, 68%). Bp 101° C. (0.95 mm Hg). $[\alpha]^{25}_D$ (CHCl$_3$)= +13.8° (c=0.78). $^1$H NMR (CDCl$_3$) δ 5.2i (1H, s), 5.15 (1H, s), 4.15 (2H, d, J=4.8 Hz), 3.98 (1H, t, J=3 Hz), 1.46 (3H, s), 1.40 (3H, s), and 1.36 (3H, s) in ppm downfield from TMS. $^{13}$C NMR (CDCl$_3$) δ 148.84, 114.21, 107.58, 79.29, 79.17, 48.07, 34.16, 33.84, 30.90, 28.70, 27.48, 26.77, and 25.04 in ppm downfield from TMS. IR (neat) 3010–2820, 1640, 1450, 1375, 1240, 1215, 1055, 995, 910, 855, and 750 cm$^{-1}$.

A minor amount of the side-product 4-R-(2-chloro-1-hydroxyisopropyl) -1-methyl-1S,2R-cyclohexanediol acetonide (0.638 g, 25%) was; also isolated and purified by its proton spectrum: (CDCl$_3$) δ 4.00 (1H, t, J=6 Hz), 3.87–3.26 (2H, m), 1.76 (3H, s), 1.57 (3H, s), and 1.23 (6H, s) in ppm downfield from TMS.

It should be noted that the enantiomeric (−)-6c is obtained by the same route but starting from the (+)-carvone.

6.18. (+)-1-Methoxy-3-methoxymethoxy-2-[2-{3'R, 4S -dihydroxyacetonide-4'-methylcyclohex-1'R -yl} prop-2-enyl]benzene ((+)-9c)

In a process analogous to that described in Section 6.16, the arylcuprate reagent derived from 7 was allowed to react with the electrophile (+)-6c. The desired compound (+)-9c was isolated as an oil in 88% yield after column chromatography. $[\alpha]^{25}_D$ (CHCl$_3$)= +12.98° (c=0.94). $^1$H NMR (CDCl$_3$) δ 7.14 (1H, t, J=8.4 Hz), 6.73 (1H, d, J=8.4 Hz), 6.58 (1H, d, J=8.4 Hz), 5.14 (2H, s), 4.73 (1H, s), 4.38 (1H, s), 3.94 (1H, doublet of d, J=6.3 and 7.5 Hz), 3.78 (3H, s), 3.43 (3H, s), 3.39 (2H, s), 1.48 (3H, s), 1.43 (3H, s), and 1.35 (3H, s) in ppm downfield from TMS. $^{13}$C NMR (CDCl$_3$) δ 158.59, 156.03, 152.15, 127.19, 117.76, 107.71, 107.28, 107.02, 104.63, 94.39, 80.01, 79.59, 56.01, 55.82, 38.43, 34.44 , 32.88, 29.14, 28.12 , 27.99, 27.65, and 25.65 in ppm downfield from TMS. IR (neat) 3030–2820, 1640, 1595, 1470, 1380, 1255, 1205, 1155, 1100, 1070, 1020, 925, 890, 780, and 740 cm$^{-1}$.

6.19. (+)-2-Hydroxy-4-methoxy-3-[2-{4'-methyl -cyclohex-3'-en-1'R-yl)prop-2-enyl]benzoic acid ((+)-22a) and ((−)-22a).

To a stirred anhydrous hexane (80 ml) solution of (+)-9b (2.000 g, 0.007 mol) and TMEDA (1.2 ml, 0.008 mol) was added dropwise a 2.15M hexane solution of n-BuLi (3.7 ml, 0.008 mol) at 0° C. The solution was stirred at 0° C. for 15 minutes and an additional 2 hours at room temperature. The lithium reagent solution was then cooled to −78° C., and a stream of anhydrous carbon dioxide gas was allowed to bubble through the solution for a period of 1 hour. The solution was exposed to the carbon dioxide for an additional 1 hour at room temperature. The reaction mixture was extracted with 5% aqueous sodium hydroxide (3×40 ml). The combined alkaline extracts was acidified with 6N hydrochloric acid and extracted with ether (3×150 ml). The combined organic extracts was then washed with brine, dried, and concentrated in vacuo. The residual oil, which contained a mixture of (+)-22a and the unhydrolyzed (+)-4-methoxy-2-methoxymethoxy-3-[2-{4'-methylcyclohex-3'-en-1'R-yl}prop-2-enyl]benzoic acid, (+)-21a, was dissolved in isopropanol (20 ml) and treated dropwise with aqueous 3N hydrochloric acid (9 ml, 0.03 mol). The solution was stirred overnight at ambient temperature. Solid sodium chloride and brine were next added, and the mixture was extracted with ether (3×60 ml). The combined organic extracts was dried and concentrated. The residue was purified by chromatography to yield pure (+)-22a (0.796 g, 40%) as a solid. Mp 163°-163.5° C. (crystals from ether/hexane). $[\alpha]^{25}_D$ (CHCl$_3$)=−52.8° (c=0.54). Anal. Calcd. for C$_{18}$H$_{22}$O$_4$: C, 71.52; H, 7.28. Found: C, 71.60; H, 7.35 ((+)-22a) and C, 71.58; H, 7.35 ((−)-22a). $^1$H NMR (CDCl$_3$) δ 10.72 (1H, S), 7.85 (1H, d, J=9 Hz), 6.52 (1H, d, J=9 Hz), 5.44 (1H, broad s), 4.70 (1H, s), 4.39 (1H, s), 3.87 (3H, s), 3.41 (2H, s), and 1.67 (3H, s) in ppm downfield from TMS. $^{13}$C NMR (CDCl$_3$) δ 175.05, 164.18, 161.45, 152.18, 133.74, 130.62, 120.91, 115.76, 106.43, 104.78, 102.84, 55.89, 40.38, 31.27, 30.78, 28.27, 27.65, and 23.50 in ppm downfield from TMS. IR (KBr) 3150-2500, 3000-2810, 1640, 1610, 1495, 1455, 1420, 1265, 1180, 1090 and 885 cm$^{-1}$. Mass spectrum (MS) m/e (% base peak) 302 (M+, 39), 284(17), 269(10), 255(15), 243(12), 216(38), 201(24), 191(23), 181(34), 163(85), 145(17), 133(30), 121(100), 104(40), 93(34), 77(29), and 67(15).

6.20. (+)-4-Methoxy-2-methoxymethoxy-3-[2-{4'-methylcyclohex-3'-en-1'R-yl}prop-2-enyl]benzaldehyde (+)-21b and ((−)-21b)

A 1.76M hexane solution of n-BuLi (3.0 ml, 5.3 mmol) was added dropwise to a stirred anhydrous ether (25 ml) solution of (+)-9b (1.230 g, 4.1 mmol) at −45° C. under a nitrogen atmosphere. The reaction mixture was stirred at low temperature for 0.5 hours and an additional 1.5 hours at room temperature. The lithium reagent solution was then cooled to −22° C., and DMF (12.6 ml, 16.3 mmol) was then added quickly and in one portion via syringe. The resulting mixture was stirred for 24 hours and then quenched with 30 ml of brine. The mixture was extracted with ether and worked up in the usual manner. The desired product (+)-21b was isolated by column chromatography as an oil (0.850 g, 64%). Some starting (+)-9b was also recovered (0.180 g, 15%). The enantiomer (−)-21b was obtained similarly using (−)-9b as the starting material. $[\alpha]^{25}_D$ (CHCl$_3$)=+48.46° (c=0.35) and −43.96° (c=0.53) for the (+) and (−) enantiomers, respectively. $^1$H NMR (CDCl$_3$) δ 10.16 (1H, s), 7.86 (1H, d, J=8 Hz), 6.80 (1H, d, J=8 Hz), 5.39 (2H, broad s), and 1.65 (3H, s). IR (neat) 3020-2815, 1675, 1590, 1430, 1380, 1275, 1255, 1160, 1065, 985, 940, 810, and 760 cm$^{-1}$. MS m/e (% base peak) 330 (M+, 298(14), 285(79), 257(12), 217(12), 203(39), 193(52), 191(44), 179(20), 175(22), 165(100), 149(13), 133(63), 121(21), 119(33), 105(56), 91(38), 77(32), and 67(13).

6.21. (+)-2-Hydroxy-4-methoxy-3-[2-{4'-methyl -cyclohex-3'-en-1'R-yl}prop-2-enyl]benzaldehyde ((+)-22b) and ((−)-22b)

Compound (+)-21b (or (−)-21b) was deprotected to the free phenol by treatment with aqueous 3N hydrochloric acid in isopropanol solution as described in Section 6.19, supra. The homochiral product (+)-22b (or (−)-22b) was obtained in ca. 92% yield as an oil after column chromatography. $[\alpha]^{25}_D$ (CHCl$_3$)=+52.8° (c=0.50) and −51.6° (c=0.45) for the (+) and (−) enantiomers, respectively. Anal. Calcd. for C$_{18}$H$_{22}$O$_3$: C, 75.52; H, 7.69. Found: C, 75.41; H, 7.78 ((+)-22b) and C, 75.57; H, 7.74 ((−)-22b). $^1$H NMR (CDCl$_3$) δ 11.44 (1H, s), 9.72 (1H, s), 7.42 (1H, d, J=8 Hz), 6.58 (1H, d, J=8 Hz), 5.42 (1H, broad s), 4.69 (1H, s), 4.39 (1H, s), 3.88 (3H, s), 3.38 (2H, s), and 1.66 (3H, s) in ppm downfield from TMS. $^{13}$C NMR (CDCl$_3$) δ 194.70, 164.48, 161.26, 151.91, 134.06, 133.74, 120.85, 115.79, 115.57, 106.6, 103.10, 55.98, 40.32, 31.23, 30.75, 28.24, 27.22, and 23.50 in ppm downfield from TMS IR (neat) 3000-2820, 1640, 1620, 1495, 1425, 1250, 1150, 1015, 890, 795, and 640 cm$^{-1}$. MS m/e (% base peak) 286(M+, 28) 268(11), 203(26), 191(13), 189(13), 177(15), 165(73), 153(15), 135(27), 121(100), 105(20), 93(29), 91(24), 79(26), 77(29), and 67(11) 6.22.

6.22. Ethyl (+)-4-methoxy-2-methoxymethoxy-3-[2-(4'-methylcyclohex-3'-en-1'R-yl}prop-2-enyl]benzoate ((+)-21c and ((−)-21c)

To a stirred anhydrous ether (100 ml) solution of (+)-9b (13.8 mmol) and TMEDA (16.6 mmol) was added dropwise 8.07 ml of a 2.05M hexane solution of n-BuLi (16.6 mmol) at 0° C. and under an inert atmosphere. The mixture was stirred at 0° for 15 minutes and an additional 1.5 hours at room temperature. Afterwards, the resulting reagent solution was cooled to −50° C. and transferred via cannula into an ethereal (50 ml) −50° C. solution of diethyl carbonate (6.41 ml, 53.0 mmol). The mixture was allowed to warm up gradually and stirred overnight at room temperature. The subsequent addition of brine and extraction with ether gave a solution which was worked up as usual. The desired ethyl ester derivative (+)-21c was obtained as an oil after chromatography (2.830 g, 60%) $[\alpha]^{25}_D$ (CHCl$_3$)=+38.6° (c=0.48). The corresponding (−)-21c isomer was obtained likewise beginning with (−)-9b. $[\alpha]^{25}_D$(CHCl$_3$)=−36.7° (c=0.56). Anal. Calcd. for C$_{22}$H$_{30}$O$_5$: C, 70.59; H, 8.02; Found: C, 70.67; H, 8.10, ((+)-21c) and C, 70.41; H, 8.11 ((−)-21c). $^1$H NMR (CDCl$_3$) δ 7.82 (1H, d, J=8 Hz), 6.68 (1H, d, J=8 Hz), 5.43 (1H, broad s), 5.03 (2H, s), 4.69 (1H, broad s ), 4.33 (2H, quartet, J=4 Hz ), 4.20 (1H, broad s), 3.85 (3H, s), 3.53 (3H, s), 3.46 (2H, s), 1.66 (3H, s), and 1.36 (3H, t, J=4 Hz) in ppm downfield from TMS. $^{13}$C NMR (CDCl$_3$) δ 165.93, 161.94, 157.32, 152.43, 133.74, 131.02, 123.43, 120.85, 117.23, 106.89, 106.14, 101.25, 76.63, 60.63, 57.62, 55.87, 31.29, 30.79, 28.88, 28.28, 23.48, and 14.37. IR (neat) 3020-2820, 1715, 1640, 1590, 1480-1430, 1260, 1140, 1070, 990, 940, and 840 cm$^{-1}$.

6.23. Ethyl (+)-2-hydroxy-4-methoxy-3-[2-{4'-methylcyclohex-3'-en-1'R-yl)prop -2-enyl]benzoate ((+)-22c) and ((−)-22c)

Following the procedure outlined in Sections 6.19 and 6.21, compound (+)-21c was converted to the free phenol (+)-22c in 88% yield $[\alpha]^{25}_D$ (CHCl$_3$)=+43.6° (c=0.36) and −41.5° (c=0.48) for the (+) and (−) enantiomers, respectively. $^1$H NMR (CDCl$_3$) δ 7.70 (1H, d, J=8 Hz), 6.38 (1H, d, J=8 Hz), 5.40 (1H, broad s), 4.63 (1H, broad s), 4.39 (1H, broad s), 4.42 (2H, quartet, J=3.6 Hz), 3.88 (3H, s), 3.34 (2H, s), 1.66 (3H, s), and 1.43 (3H, t, J=3.6 Hz). IR (neat) 3080, 2980-2810, 1660, 1610, 1500, 1370, 1275, 1180, 1095, 1030, 890, 785, and 755 cm$^{-1}$. MS m/e (% base peak) 330 (M+16), 284(12), 216(20) 209(53), 191(24) 188(27), 163(90), 133(22), 121(100), 105(26), 91(18), 77 (17), and 67 (12).

6.24. Ethyl (+)-4-methoxy-2-methoxymethoxy-3-[2-{3'R, 4'S-dihydroxyacetonide-4'-methylcyclohex-1'R-yl)prop-2-enyl]benzoate ((+)-25c)

Following the procedure outlined in Section 6.19, a hexane/TMEDA solution of (+)-9c was treated with n-BuLi. Diethyl carbonate (4-fold excess) was used as the electrophile, and the product (+)-25c was isolated after work up and chromatography in 46% yield. Unreacted (+)-9c was also recovered (15%). $[\alpha]^{25}_D$ (CHCl$_3$)=+13.08 (c=0.91). $^1$H NMR (CDCl$_3$) δ 7.83 (1H, d, J=8.5 Hz), 6.69 (1H, d, J=8.5 Hz), 4.98 (2H, s), 4.71 (1H, s), 4.27 (2H, quartet, J=5.5 Hz), 4.24 (1H, s), 3.91 (1H, t, J=6.3 Hz), 3.74 (3H, s), 3.47 (3H, s), 3.38 (2H, broad s), 1.37 (3H, s), 1.30 (3H, s), and 1.25 (3H, s) in ppm downfield from TMS.

6.25. (+)-4-Methoxy-2-methoxymethoxy-3-[2-{3'R,4'S-dihydroxyacetonide -4'-methylcyclohex-1'R-yl)prop-2-enyl]benzaldehyde ((+)-25b)

The compound (+)-9c was lithiated as in the preceding section and allowed to react with a 4-fold excess of ethyl formate at −50° C. The product (+)-25b was obtained in 53% yield after work up and purification. Some unreacted (+)-9c (17%) was also recovered. ¹H NMR (CDCl₃) δ 7.80 (1H, d, J=8.5 Hz), 6.80 (1H, d, J=8.5 Hz), 5.03 (2H, s), 4.80 (1H, s), 4.30 (1H, s), 3.98 (1H, t, J=6.5 HZ), 3.87 (3H, s), 3.56 (3H, s), 3.39 (2H, s), 1.50 (3H, s), 1.43 (3H, s) and 1.36 (3H, s) in ppm downfield from TMS.

6.26. (+)-2-Hydroxy-4-methoxy-3-[2-{3'R, 4'S-dihydroxy-4'-methylcyclohex -1'R-yl}prop-2-enyl]benzaldehyde ((+)-26b) and Ethyl (+)-2-hydroxy-4-methoxy-3-[2-{3'R 4'S-dihydroxy-4'-methylcyclohex-1'R-yl)prop-2-enyl]benzoate ((+)-26c)

The acetonide and methoxymethyl protecting groups are removed from compounds (+)-25b and (+)-25c by stirring each in the presence of aqueous 3N hydrochloric acid in

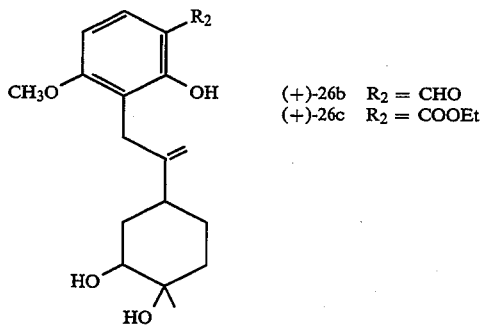

(+)-26b  R₂ = CHO
(+)-26c  R₂ = COOEt isopropanol solution as described in Section 6.19 to yield the free diol/phenol (+)-26b and (+)-26c, respectively.

6.27. (+)-7-Carboxyl4--methoxy-2-methyl-2-[4'-methylcyclohex-3'-en-1'R-yl]-(3H)-benzofuran ((+)-20a) and ((−)-20a)

Amberlyst A-15 (3.170 g), which had been dried at 110° C. (30 mm Hg) overnight, was added to an anhydrous methylene chloride (32 ml) solution of (+)-22c (0.470 g, 1.56 mmol) at ambient temperature. After stirring for 30 minutes, the cyclization was essentially complete as monitored by TLC. The mixture was filtered, and the resin was washed several times with fresh ether. The filtrates were combined and concentrated in vacuo. The residue was purified by chromatography and provided 0.362 g (77%) of the desired dihydrobenzofuran (+)-20a. The (−)-20a was obtained similarly beginning with (−)-22c. Mp 142°-144° C. and 131°-135° C. for (+)-20a and (−)-20a, respectively [α]²⁵_D (CHCl₃)=4.0° (c=0.20) and 1.56° (c=0.44) for the (+) and (−) isomers, respectively. Anal. Calcd. for C₁₈H₂₂O₄: C, 71.52; H, 7.28. Found: C, 71.49; H, 7.39 ((+)-20a) and c, 71.47; H, 7.38 ((−)-20a). ¹NMR (CDCl₃) δ 7.86 (1H, d, J=9 Hz), 6.52 (1H, d, J=9 Hz), 5.38 (1H, broad s), 3.89 (3H, s), 3.17-2.79 (2H, m), 1.65 (3H, s), and 1.49 (3H, s) in ppm downfield from TMS. ¹³C NMR (CDCL₃) δ 165.88, 160.33, 159.44, 134.16, 132.83, 119.62, 114.02, 105.69, 104.25, 96.76, 55.70, 43.30, 36.16, 30.39, 26.57, 24.51, 23.87, and 23.33 in ppm downfield from TMS. IR (KBr) 3300-2500, 3000-2820, 1670, 1620, 1440, 1270, 1100, and 770 cm⁻¹. MS m/e (% base peak) 302 (M⁺, 55), 284(17), 207(22), 191(58), 181(19), 163(68), 147(14), 135(40), 121(100), 105(31), 93(25), and 77(26).

Also recovered were small amounts of starting material (5%) and a side-product, 3,4-dihydro-5-methoxy-8-carboxy-3-(4'-methylcyclohex-3-en-1'R-yl)-(2H)-benzopyran, 28a (11%), identified by its proton spectrum: (CDCl₃) δ 8.05 (1H, d, J=8 Hz), 6.55 (1H, d, J=8 Hz), 5.35 (1H, broad s), 3.90 (3H, s), and 1.71 (3H, s) in ppm downfield from TMS.

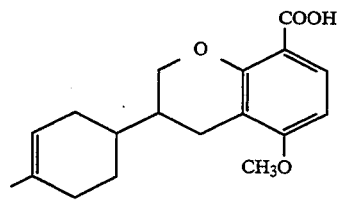

6.28. (+)-7-Formyl -4-methoxy-2-methyl-2-[4'-methylcyclohex-3'-en-1'R-yl ]-(3H)-benzofuran ((+)-20b) and ((−)-20b)

The precursor (+)-22b or (−)-22b was treated with Amberlyst A-15 (2 g resin/mmol substrate) as described in the preceding section except that the reaction mixture was stirred for at least 3 hours. The mixture was worked up as described previously and provided (+)-20b or (−)-20b, as the case may be, as a viscous, easily oxidizable oil in 73% yield. Anal. Calcd. for C₁₈H₂₂O₃: C, 75.52; H, 7.69 Found: C, 75.31; H, 7.76 ((+)-20b) and C, 75.26; H, 7.79 ((−)-20b). ¹H NMR (CDCl₃) δ 10.34 (1H, s), 7.64 (1H, d, J=8 Hz), 6.45 (1H, d, J=8 Hz), 3.88 (3H, s), 3.11-2.69 (2H, m), 1.65 (3H, s), and 1.44 (3H, s) in ppm downfield from TMS. ¹³C NMR (CDCl₃) δ 187.47, 163.38, 161.36, 134.10, 129.18, 119.92, 11.4.57, 103.58, 94.74, 55.63, 43.41, 35.91, 35.22, 30.49, 26.55, 24.64, 23.74 and 23.35 in ppm downfield from TMS, IR (neat) 3000-2800, 1675, 1610, 1500, 1430, 1390, 1285, 1270, 1205 1100 1060 885 and 790 cm⁻¹.

6.29. (+)-7-Carbethoxy-4-methoxy-2-methyl -2-[4'-methylcyclohex-3'-en-1'R-yl]-(3H)-benzofuran ((+)-20c) and ((−)-20c)

Following the procedure of Section 6.27, precursor (+)-22c was stirred in a methylene chloride suspension of Amberlyst A-15 resin (1 g resin/mmol substrate) for 24 hours. The usual work up and purification steps gave the cyclized product (+)-20c in 81% yield. The corresponding isomer (−)-20c was obtained in a similar fashion beginning with precursor (−)-22c. ¹H NMR (CDCl₃) δ 7.74 (1H, d, J=8 Hz), 6.38 (1H, d, J=8 Hz), 5.38 (1H, broad s), 4.31 (2H, m), 3.86 (3H, s), 3.14-2.69 (2H, m), 1.67 (1H, s), 1.42 (3H, s), and 1.34 (3H, t, J=4 Hz) in ppm downfield from TMS. ¹³C NMR (CDCl₃) δ 165.29, 161.42, 159.78, 133.92, 131.95, 120.26, 115.03, 107.03, 93.36, 60.04, 55.44, 43.47, 36.37, 30.59, 26.54, 24.25, 23.36, and 14.41 in ppm downfield from TMS. IR (neat) 3000-2815, 1715, 1690, 1650, 1610, 1495, 1430, 1270, 1100, 1030, 890, and 770 cm⁻¹. MS m/e (% base peak) 330 (M⁺, 20), 285(14), 273(18), 209(37), 191(29), 163(100), 147(13), 133(13), 121(68), 105(18), and 77(13).

6.30. (+)-7-Formyl-4-methoxy-2-methyl-2-[3'R,4'S-dihydroxy-4'-methylcyclohex -1'R-yl]-(3H)-benzofuran ((+)-27b), (+)-7-carbethoxy-4-methoxy-2-methyl-2-

[3'R,4'S-dihydroxy-4'-methylcyclohex -1'R-yl]-(3H)-benzofuran ((+)-27c), and (+)-7-carboxyl-4-methoxy-2-methyl-2-[3'R,4'S-dihydroxy-4'-methylcyclohex -1,R-yl]-(3H)-benzofuran ((+)-27a)

The cyclization of compounds (+)-26b and (+)-26c which were described in Section 6.26, is accomplished by the procedures described in the preceding sections to give dihydrobenzofurans (+)-27b and (+)-27c, respectively. The 7-carboxylic acid derivative, (+)-27a, may be obtained by alkaline hydrolysis of (+)-27c.

6.31. (+)-7-Formyl-4-hydroxy-2-methyl -2-[4'-methylcyclohex-3'-en-1'R-yl]-(3H)-benzofuran ((+)-23b) and ((−)-23b)

Compound (+)-20b (0.200 g, 0.70 mmol), described in Section 6.28, was dissolved in 3 ml of anhydrous ether/HMPA (2:1, v/v) under an atmosphere of dry nitrogen. The solution was cooled (−22° C.) and treated with an HMPA (3.7 ml) solution of t-BuSLi (1.40 mmol). The reaction mixture was allowed to warm up gradually and stirred at room temperature for 48 hours. The reaction was then quenched with brine (15 ml) and extracted with ether (4×60 ml). The combined extracts were worked up in the usual manner (i.e., dried, concentrated, and chromatographed) yielding the desired product (+)-23b (0.183 g, 95%) as a solid. The product (−)-23b was obtained likewise beginning with(−)-20b. Mp 70°-74° C. for both diastereomeric compounds. Anal. Calcd. for $C_{17}H_{20}O_3$: C, 75.00; H, 7.35. Found: C, 74.85; H, 7.41 ((+)-23b) and C, 74.90; H, 7.50 ((−)-23b). $^1$H NMR (CDCl$_3$) δ 9.94 (1H, s), 8.91 (1H, broad s), 7.52 (1H, d, J=8 Hz), 6.49 (1H, d, J=8 Hz), 5.37 (1H, s), 3.19–2.74 (2H, m), 1.64 (3H, s), and 1.44 (3H, s) in ppm downfield from TMS. $^{13}$C NMR (CDCl$_3$) δ 188.84, 165.02, 160.48, 134.10, 129.50, 119.89, 113.31, 112.97, 109.72, 95.25, 43.37, 35.51, 30.46, 26.55, 24.67, 23.73, and 23.35 in ppm downfield from TMS. IR (KBr) 3500–3150, 2980–2820, 1640, 1590, 1445, 1255, 1210, 1160, 1040, and 800 cm$^{-1}$. MS m/e (% base peak) 272 (M$^+$, 52), 254(7), 204(9), 189(26), 177(42), 165(15), 151(71), 139(17), 121(100), 105(23), 93(53), 77(34), and 67(14).

6.32. (+)-7-Carbethoxy-4'-hydroxy-2-methyl -2-[4'-methylcyclohex-3'-en-1'R-yl]-(3H) -benzofuran ((+)-23c) and (−)-23c)

To a stirred solution of (+)-20c (0.600 g, 1.82 mmol) dissolved in 9 ml of an ether/HMPA solvent mixture (2:1, v/v) was added dropwise, at −22° C., 9.0 ml of a 0.4M HMPA solution of t-BuSLi (3.5 mmol, 1.9 equiv) under a nitrogen atmosphere. The mixture was allowed gradually to warm up to ambient temperature and stirred for 3 days. Brine and ether were added subsequently and the mixture extracted with fresh portions of ether. The organic layers were combined and worked up in the usual manner providing 0.534 g (97%) of (+)-23c as a solid. Once again, the (−)-23c was prepared from the (−)-20b precursor. Mp 53°-57° for both diastereomeric products. $^1$H NMR (CDCl$_3$) δ 7.61 (1H, d, J=8 Hz), 7.32 (1H, broad s), 6.38 (1H, d, J=8 Hz), 5.36 (1H, broad s), 4.32 (2H, m), 3.11–2.62 (2H, m), 1.63 (3H, s), 1.39 (3H, s), and 1.34 (3H, t, J=4 Hz) in ppm downfield from TMS. $^{13}$C NMR (CDCl$_3$) δ 166.02, 162.35, 157.52, 133.96, 131.56, 120.13, 113.71, 108.02, 105.48, 93.79, 60.30, 43.37, 35.71, 30.55, 26.37, 24.48, 23.76, 23.36, and 14.36 in ppm downfield from TMS. IR (KBr) 3200, 2990–2840, 1680, 1600, 1445, 1270, 1050, 890, and 790 cm$^{-1}$.

6.33. (+)-7-Carboxyl-4-hydroxy-2-methyl -2-[4'-methylcyclohex-3'-en-1'R-yl]-(3H)-benzofuran ((+)-23a) and ((−)-23a)

A mixture of (+)-23c (0.210 g, 0.66 mmol) and aqueous 30% sodium hydroxide (1 ml) dissolved in ethyl alcohol (5 ml) was heated under reflux overnight. The mixture was then cooled to 0° C. and acidified to pH=1 with 3N hydrochloric acid. Brine (10 ml) and ether (50 ml) were added, and the mixture was extracted with fresh ether (3×50 ml). The extracts were combined and worked up as usual. Chromatography provided 0.168 g (88%) of (+)-23a as a high-melting solid. Alkaline hydrolysis of (−)-23c gave (−)-23a as expected. Mp 228°-231° C. (with decomposition) for both products. $^1$H NMR (acetone-d$_6$) δ 7.50 (1H, d, J=8 Hz), 6.38 (1H, d, J=8 Hz), 5.32 (1H, broad s), 3.33–2.70 (2H, m), 1.60 (3H, s), and 1.36 (3H, s). IR (KBr) 3500–3380, 2980–2810, 1650, 1630, 1595, 1490, 1455, 1280, 1040, 880, and 780 cm$^{-1}$.

6.34. (+)-7-Formyl-4-hydroxy-2-methyl -2-[3'R,4'S-dihydroxy-4'-methyl -cyclohex-1'R-yl]-(3H)-benzofuran ((+)-24b) and (+)-7-carbethoxy -4-hydroxy-2-methyl-2-[3'R, 4'S -dihydroxy-4'-methylcyclohex -1'R-yl]-(3H)-benzofuran ((+)-24c)

Following the procedure outlined in Section 6.31, except that 6.0 equiv of the t-BuSLi reagent is used, compounds (+)-27b and (+)-27c are demethylated to give 4-hydroxy derivatives (+)-24b and (+)-24c, respectively.

6.35. (+)-7-Carboxyl-4-hydroxy-2-methyl -2-[3'R,4'S-dihydroxy-4'-methyl cyclohex-1'R-yl]-(3H)-benzofuran ((+)-24a)

The 7-carbethoxy derivative, (+)-24c, described in the preceding section, is hydrolyzed as prescribed in Section 6.33 to give the free carboxylic acid product, (+)-24a.

6.36. Complement Inhibition

The dihydrobenzofuran and spirobenzofuran cyclohexane compounds of the general formulae 3, 4, the synthetic intermediates of the general formula 5, and the salts thereof of the present invention were assayed for their ability to inhibit complement by the methods described infra.

6.36.1. Demonstration of Inhibition of C3a and C5a Production

The ability to inhibit complement was tested by assaying for specific inhibition of C3a and C5a production. For all experiments, a single human serum pool, to be used as a source of complement, was aliquoted and stored frozen at −70° C. Human IgG was heat-aggregated, aliquoted, and stored frozen at −70° C. For each experiment, serum aliquots were equilibrated at 37° C. with varying concentrations of the compounds tested. The classical complement pathway was initiated by the addition of aggregated human IgG. Control samples containing no IgG were always included. After a fixed reaction time of 10 minutes (determined in an earlier time-course study to provide a convenient time interval during which the production of C5a or C3a is nearly complete, i.e., greater than 90%), the levels of the released complement peptides (C5a or C3a) were determined by radioimmunoassay using commercially available radioimmunoassay (RIA) kits (C5a RIA, UpJohn Cat. No. 3250-02; C3a RIA, UpJohn Cat. No. 3245-01; C5a RIA, Amersham Cat. No. RPA. 520; C3a RIA, Amersham RPA. 518) in modified procedures.

Since a competitive immunoassay was used, complement peptide (C5a and C3a) concentrations varied inversely with the counts. The Counts Bound (CB) for a sample was defined as the total counts (in counts per minute, cpm) measured in the pellet minus the counts measured in a non-specific binding (NSB) control. The NSB control was a sample containing only tracer peptide ($^{125}$I-labelled) and second precipitating antiserum; it contained no C5a-or C3a-specific antiserum.

The y-axis in FIG. 2 represents the fraction inhibition. The fraction inhibition is equal to the Counts Bound (CB) for a "sample," less the CB in the "sample with no added compound," divided by the CB for the "no IgG control" less the CB in the "sample with no added compound."

$$\text{INHIBITION} = \frac{[(CB \text{ sample}) - (CB \text{ no compound})]}{[(CB \text{ no } IgG) - (CB \text{ no compound})]}$$

When C5a production is inhibited at concentrations of added compound at which C3a production is unaffected, the data suggest that complement inhibition is directed toward the C5 activation step. FIG. 2 is representative of the data plots obtained from the assays described above. The results are summarized in Table VI and demonstrate that the complement inhibition activities exhibited by some of the compounds appear to be directed toward inhibition of C5 activation, and that the inhibitory activities are comparable to that of K-76 COONa itself.

TABLE VI

IN VITRO COMPLEMENT INHIBITION IN HUMAN SERUM

| Compound | IC$_{50}$ (mM)$^a$ | |
|---|---|---|
| | C3a | C5a |
| (+)—22a | 11 | 6 |
| (+)—20a | >14$^b$ | 8 |
| (−)—20a | 11 | 6 |
| (+)—23a | >14$^b$ | >14$^b$ |
| 12b | 18 | 9 |
| 12a | 13 | 8 |
| 11a | 22 | 5 |
| K-76 COONa | —$^c$ | 3 |

$^a$The concentration of compound required to inhibit C3a or C5a production 50% relative to control samples which contained no test compound.
$^b$The inhibition observed at this concentration was less than about 50%.
$^c$Only marginal inhibition was observed at a concentration of about 8.5 mM.

6.36.2. Demonstration of Inhibition of Complement-Mediated Hemolysis

The ability to inhibit complement was also tested by assaying for inhibition of complement-mediated red cell lysis (hemolysis). The inhibition of hemolysis was determined as a function of compound concentration. The compounds to be tested were diluted in 0.1M Hepes buffer (0.15N NaCl, pH 7.4), and 50 μl were added to each well of a V-bottom microtiter plate. Human serum, used as the complement source, was diluted 1 to 500 in Hepes buffer, and 50 μl were added to each well. Next, commercially available sheep erythrocytes with anti-sheep antibody (Diamedix Cat. No. 789-001) were used as received and added at 100 μl/well to initiate the complement pathway leading to hemolysis. The plate was incubated for 60 minutes at 37° C. and then centrifuged at 500×g for 10 minutes. The supernatants were removed and placed in a flat-bottom microtiter plate. The extent of hemolysis was measured as a function of the sample absorbance at 410 nm. The maximal absorbance (corresponding to maximal hemolysis), $A_{max}$, was obtained from the absorbance value of an erythrocyte sample containing only human serum, $A_s$, less the absorbance of a sample containing only the red cells, $A_0$. Thus, $A_{max} = A_s - A_0$. The difference between the absorbance of an erythrocyte sample containing both human serum and inhibitive compound, and the absorbance of a cell sample containing inhibitive compound only, was defined as $A_{sample}$. The inhibition, IH, was expressed as the fraction $(A_{max} - A_{sample})/A_{max}$, and IH$_{50}$ was defined as the concentration of inhibitive compound required to produce a value of IH=½.

FIG. 3 shows the plot of inhibition, IH, versus the concentration of 11a added to the cell samples. The concentration of 11a corresponding to IH$_{50}$ is approximately 0.9 mM. Table VII summarizes the results of several assays using some of the compounds of the present invention and shows their effectiveness in inhibition of hemolysis.

TABLE VII

INHIBITION OF COMPLEMENT-MEDIATED HEMOLYSIS

| Compound | IH$_{50}$ (mM)* |
|---|---|
| 11a | 0.9 |
| 12a | 1.6 |
| 14a | >2.8 |
| 15a | 0.7 |
| (+)—20a | 0.7 |
| (−)—20a | 0.3 |
| (+)—23a | 2.1 |
| (−)—23a | 2.4 |
| 30a | 0.6 |
| 31a | 1.3 |
| K-76 COONa | 0.3 |

*The concentration of compound required to produce a value for hemolysis inhibition (IH, as defined supra in Section 6.36.2) of ½.

6.37. Immunosuppressive Activities

The dihydrobenzofuran and spirobenzofuran cyclohexane compounds of the general formulae 3, 4, intermediates 5, and the salts thereof of the present invention were tested for their ability to inhibit cell-mediated immune activity. The specific activities demonstrated by the tested compounds included the inhibition of natural killer (NK) activity, the inhibition of peripheral blood lymphocyte (PBL) proliferation, and the inhibition of cell surface interleukin-2-receptor expression as described infra. In addition, the ability of compound 11a to inhibit the proliferation of Chinese hamster ovary (CHO) cells was tested; no inhibition of CHO cells was observed, suggesting that the compound's inhibitory activities were specific to the lymphoid cells of the immune system. The experiments were conducted using in vitro assays for determining dose-dependent effects of the compounds of the invention on immune function.

6.37.1. Demonstration of Inhibition of Natural Killer Activity

Compounds were tested for their effects on the ability of peripheral blood mononuclear cells to lyse NK-sensitive target cells, K562. NK activity was determined using $^{51}$Cr-labeled K562 erythromyeloid leukemia cells as targets, and normal peripheral blood mononuclear cells as effector cells, in a four hour cytotoxicity assay. Effector cells were isolated from fresh blood by Ficoll-Hypaque gradient centrifugation, and 100 μl of a 5×10$^5$ cell/well suspension were added to each well of a V-bottom microtiter plate. The compound 11a was diluted in RPMI 1640 medium containing 10% fetal calf serum and dispensed at 100 μl per well. Target cells (K562) were/labeled for 30 minutes with 100 μCi of $^{51}$Cr, washed thoroughly and dispensed in a 20 μl volume at 10$^4$ cells/well. These cell concentrations resulted in an effector-to-target cell ratio of 50:1. The microtiter plate was centrifuged at 50×g for 5 minutes and incubated in a humidified chamber with 5% $CO_2$ at 37° C. After 4 hours, 100 μl were removed from each well and the radioactivity was measured with a LKB 1275 gamma counter. The percent specific lysis was calculated as follows:

% specific lysis = [(EXP−SR)/(TOTAL−B)] × 100 where EXP (experimental value) was obtained using effector and target cells; SR (the spontaneous release) was obtained from target cells incubated with media alone; TOTAL release was obtained by hypotonic lysis in water; and B represents instrumental background. Means were calculated from quadruplicate wells and the standard deviations never exceeded 10%. Viability of the effector cells incubated with the test compound was determined by trypan blue exclusion.

The results of the inhibition of natural killer activity for 7-carboxy-4-methoxyspiro[benzofuran-2(3H)-cyclohexane] (11a) sodium salt are summarized in Table VIII.

TABLE VIII

INHIBITION OF NATURAL KILLER ACTIVITY BY 7-CARBOXY-4-METHOXYSPIRO[BENZOFURAN-2(3H)-CYCLOHEXANE] (11a), SODIUM SALT

| (11a) Concentration (mM) | % Specific Lysis | Spont. Release Target Cells Alone (K562) | % Viability of Effector Cells[a] |
|---|---|---|---|
| 0 | 17 | 6 | 95 |
| 0.4 | 7 | 5 | 95 |
| 0.8 | 4 | 5 | 95 |
| 1.6 | 1 | 5 | 95 |
| 3.2 | −1 | 5 | 76 |
| 6.4 | 18 | 23 | 5 |

[a]Viability was determined by trypan blue exclusion.

The data listed in Table VIII indicate that compound 11a can, at appropriate concentrations, effectively inhibit natural killer activity.

6.37.2. Demonstration of Inhibition of Proliferation of Peripheral Blood Lymphocytes The proliferation of human peripheral blood lymphocytes (PBL) in response to phytohemagglutinin (PHA, Wellcome) or anti-CD3 monoclonal antibody (OKT-3, Ortho) was assessed by the incorporation of $^3$H-thymidine. Compound 11a was diluted in culture media to the desired concentrations, human PBL were added to a final concentration of $10^6$ cells/ml, and then either PHA (Wellcome) or anti-CD3 (OKT3, Ortho) antibody (final concentration, 1 mg/ml) was added to initiate proliferation. The final volume per sample was 100 μl. The cells were incubated for 72 hours after stimulation, pulsed with 1 μCi $^3$H-thymidine per sample for 4 hours, harvested, and counted in a scintillation counter.

Separate experiments, conducted on samples exposed only to varying amounts of 11a without the stimulant, showed that the PBL were viable, as determined visually by trypan blue exclusion, in the concentration ranges of 11a used above.

The results (FIGS. 4, 5) showed that compound 11a inhibited PBL proliferation in a dose-dependent manner. Half-maximal inhibition was observed at about 0.5 mM of 11a when cultures were stimulated with either PHA (FIG. 4) or anti-CD3 antibody (FIG. 5). Because cell viability was unaffected by the presence of 11a (see supra), the inhibition apparently was not due to cytotoxic effects.

Additional compounds of the invention were tested for their immunosuppressive activities, with the results presented in Table IX.

TABLE IX

INHIBITION OF PROLIFERATION OF PERIPHERAL BLOOD LYMPHOCYTES

| | $IP_{50}$ (mM)[a] | |
|---|---|---|
| Compound | PHA-stimulated PBL | OKT-3-stimulated PBL |
| 11a | 0.4 | 0.5 |
| 15a | 0.7 | 0.4 |
| (+)−20a | 2.1 | 1.7 |
| (−)−23a | 2.8 | 2.0 |
| K-76 COONa | 0.5 | 0.5 |

[a]The concentration of compound required to inhibit PBL proliferation 50% relative to control samples which contained no test compound.

The results (Table IX) revealed that each of the tested compounds inhibited PBL proliferation.

Release of cell surface interleukin-2-receptor (IL-2R) or CD8 antigen from lymphocytes is a correlate of T cell activation (Rubin et al. J. Immunol. 1985, 135, 3172–77; Rubin et al. Fed. Proc. 1985 44, 946; Fujimoto, J. et al. J. Exp. Med. 1983, 159, 752–66; Tomkinson, B. et al. 2d Annual Conference on Clinical Immunol. Washington, D.C., Oct. 30, 1987). In some experiments, the level of IL-2R or CD8 protein released into the supernatant of the PBL cultures was assessed by removing aliquots therefrom just prior to pulsing with $^3$H-thymidine. Commercially available enzyme immunoassay kits (CELLFREE™ IL-2R, Cat. No. CK1020, T Cell Sciences, Inc., Crambridge, Mass., or CELLFREE™ T8/CD8, Cat. No. CK1040, T Cell Sciences) were used to determine the levels of the two analytes. The results using compound 11a showed that 11a was an inhibitor of both IL-2R (FIG. 6) and CD8 (FIG. 7) protein release, in stimulated PBL cultures.

6.37.3. Demonstration of Inhibition of Cell Surface Interleukin-2 Receptor Expressions The interleukin-2-receptor (IL-2R) is not detectable on the surface of resting T cells. Upon activation by specific antigens or mitogens, T cell proliferation is mediated by an autocrine mechanism whereby activated cells secrete interleukin-2-and express cell surface IL-2R (Meuer, S. C. et al. Proc. Natl. Acad. Sci. U.S.A. 1984, 81, 1509;Tsudo, M., et al. J. Exp. Med. 1984, 160, 612–617; Waldmann, T. A., et al. J. Exp. Med. 1984, 160, 1450–1466).

Compounds were tested for their ability to inhibit T cell activation, as indicated by inhibition of cell-surface IL-2R expression. PBL cultures (1.5 ml; 24-well plates) were stimulated with PHA (1 μg/ml) for 72 hours in the absence or presence of varying amounts of compound 11a. Subsequently, the cells were stained using fluorescein isothiocyanate (FITC)-labeled anti-IL-2R antibody (Act-T-Set IL-2R, Cat. No. AA2009, T Cell Sciences, Inc., Cambridge, Mass.) and analyzed by flow cytometry (Ortho System 30) (Table X).

TABLE X

INHIBITION OF CELL SURFACE IL-2R EXPRESSION BY 7-CARBOXY-4-METHOXYSPIRO[BENZOFURAN-2(3H)-CYCLOHEXANE] (11a), SODIUM SALT

| Concentration of 11a (mM) | Number of Cells Positive for IL-2R | Percentage Positive[a] |
|---|---|---|
| 0 | 4845 | 96.9 |
| 0.44 | 913 | 18.3 |

| TABLE X-continued |||
|---|---|---|
| INHIBITION OF CELL SURFACE IL-2R EXPRESSION BY 7-CARBOXY-4-METHOXYSPIRO[BENZOFURAN-2(3H)-CYCLOHEXANE] (11a), SODIUM SALT |||
| Concentration of 11a (mM) | Number of Cells Positive for IL-2R | Percentage Positive[a] |
| 1.76 | 225 | 4.5 |

[a]Based upon a total cell count of 5000.

The results listed in Table X indicate a dramatic reduction in the number of PBL expressing the IL-2R in the presence of 11a. We also observed that the amount of IL-2R cell surface expression was reduced in the presence of 11a. The data thus demonstrate that compound 11a significantly suppresses IL-2R cell-surface expression, indicating that this compound can effectively inhibit T cell activation in PBL cultures.

6.37.4. Lack of Inhibition of CHO Cell Proliferation

The specificity of compound 11a's inhibitory activity upon immune cells was demonstrated by assaying for 11a's ability to inhibit the proliferation of Chinese hamster ovary (CHO) cells.

Non-confluent CHO cells were allowed to proliferate for 4 hours in a 96-well plate at a volume of 50 μl per well in the absence or presence of compound 11a at a concentration of 1.8 mM. The cells were pulsed with 0.5 μCi of $^3$H-thymidine per sample for 4 hours, harvested, and the amount of incorporated $^3$H-thymidine was determined by scintillation counting. The CHO cells allowed to proliferate in the absence of added compound yielded a value of 57025 (±7530) CPM. The value for the sample grown in the presence of 11a was 52549 (±6272) CPM. These values revealed no statistical difference in the proliferation rate of the two samples. Because the CHO cell line is of the non-lymphoid type, this result suggests that the compounds of the present invention do not generally inhibit mammalian cell proliferation, but inhibit activation and/or proliferation of PBL cultures.

What is claimed is:

1. A pharmaceutical composition for the treatment of a patient with an immune disorder or a disorder involving undesirable or inappropriate complement activity comprising an amount of a compound effective to treat an immune disorder involving undesirable or inappropriate complement activity wherein said compound has the general formula, 4:

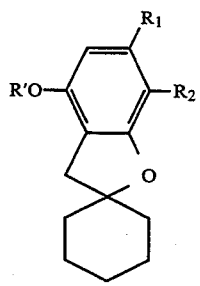

in which R is a hydrogen atom or a lower alkyl group; $R_1$ is a hydrogen atom; a carboxyl group, a formyl group, a hydroxymethyl group, an N- (lower alkyl) carboxamide group, a trifluoroacetyl group, a carbalkoxy group, a halide group, a substituted vinyl group of 2-10 carbon atoms, or an alkylidene group of 2-20 carbon atoms, with the proviso that $R_1$ is a hydrogen atom when $R_2$ is a carboxyl group, a formyl group, a hydroxymethyl group, an N-(lower alkyl) carboxamide group, a trifluoroacetyl group, a carbalkoxy group, a halide group, a substituted vinyl group of 2-10 carbon atoms, or a alkylidene group of 2-20 carbon atoms; $R_2$ is a hydrogen atom, carboxyl group, a formyl group, a hydroxymethyl group, a halide group, a substituted vinyl group of 2-10 carbon atoms, or a alkylidene group of 2-20 carbon atoms, with the proviso that $R_2$ is a hydrogen atom when $R_1$ is a carboxyl group, a formyl group, a hydroxymethyl group, an N-(lower alkyl) carboxamide group, a trifluoroacetyl group, a carbalkoxy group, a halide group, a substituted vinyl group of 2-10 carbon atoms, or an alkylidene group of 2-20 carbon atoms; or a pharmaceutically acceptable salt thereof.

2. The pharmaceutical composition of claim 1 in which said compound is 7-carboxyl-4-methoxyspiro{benzofuran-2(3H)-cyclohexane} or a pharmaceutically acceptable salt thereof.

3. The pharmaceutical composition of claim 1 in which said compound is 6-carboxyl-4-methoxyspiro{benzofuran-2(3H)-cyclohexane} or a pharmaceutically acceptable salt thereof.

4. The pharmaceutical composition of claim 1 in which said compound is 7-formyl-4-methoxyspiro{benzofuran-2(3H)-cyclohexane}.

5. The pharmaceutical composition of claim 1 in which said compound is 4-methoxyspiro{benzofuran 2-(3H)-cyclohexane}-7-N-methylcarboxamide.

6. The pharmaceutical composition of claim 1 in which said compound is 4-methoxyspiro{benzofuran-2(3H)-cyclohexane}-7-N-tert-butylcarboxamide.

7. The pharmaceutical composition of claim 1 in which said compound is 7-carboxyl-4-hydroxyspiro{benzofuran-2-(3H)-cyclohexane} or a pharmaceutically acceptable salt thereof.

8. The pharmaceutical composition of claim 1 in which said compound is 7-formyl-4-hydroxyspiro{benzofuran-2(3H)-cyclohexane}.

9. The pharmaceutical composition of claim 1 in which said compound is 6-formyl-4-methoxyspiro{benzofuran-2(3H)-cyclohexane}.

10. The pharmaceutical composition of claim 1 in which said compound is 6-carboxyl-4-hydroxyspiro{benzofuran-2(3H)-cyclohexane} or a pharmaceutically acceptable salt thereof.

11. The pharmaceutical composition of claim 1 in which said compound is 6-formyl-4-hydroxyspiro{benzofuran-2-(3H)-cyclohexane}.

12. A pharmaceutical composition for the treatment of a patient with an immune disorder or a disorder involving undesirable or inappropriate complement activity comprising an mount of a compound effective to treat an immune disorder involving undesirable or inappropriate complement activity wherein said compound has the general formula, 4:

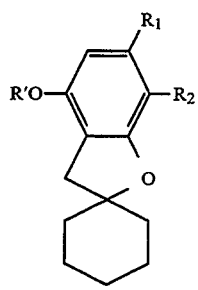

in which R is a hydrogen atom or a lower alkyl group; R₁ is hydrogen a carboxyl group, a formyl group, a hydroxymethyl group, an N-(lower alkyl) carboxamide group, a trifluoroacetyl group, a carbalkoxy group, a halide group, a substituted vinyl group of 2–10 carbon atoms, or an alkylidene group of 2–20 carbon atoms; or a pharmaceutically acceptable salt thereof.

13. The pharmaceutical composition of claim 1 in which R is hydrogen.

14. The pharmaceutical composition of claim 12 in which R is hydrogen.

15. The pharmaceutical composition of claim 1 in which R is a lower alkyl.

16. The pharmaceutical composition of claim 12 in which R is a lower alkyl.

17. The pharmaceutical composition of claim 1 in which R₁ is hydrogen.

18. The pharmaceutical composition of claim 1 in which R₂ is hydrogen.

* * * * *